(12) United States Patent
Davis et al.

(10) Patent No.: US 8,501,291 B2
(45) Date of Patent: *Aug. 6, 2013

(54) STERILIZED POLYETHERIMIDE/POLYPHENYLENE ETHER SULFONE ARTICLES

(75) Inventors: Scott Michael Davis, Pittsfield, MA (US); Robert R. Gallucci, Mt. Vernon, IN (US); Shawn Lee, Dalton, MA (US); Mark A. Sanner, Evansville, IN (US)

(73) Assignee: Sabic Innovative Plastics IP B.V. (NL)

( * ) Notice: Subject to any disclaimer, the term of this patent is extended or adjusted under 35 U.S.C. 154(b) by 0 days.

This patent is subject to a terminal disclaimer.

(21) Appl. No.: 13/486,425

(22) Filed: Jun. 1, 2012

(65) Prior Publication Data

US 2012/0308777 A1 Dec. 6, 2012

Related U.S. Application Data

(60) Provisional application No. 61/493,140, filed on Jun. 3, 2011.

(51) Int. Cl.
*B29D 22/00* (2006.01)

(52) U.S. Cl.
USPC ......... 428/35.7; 428/34.1; 525/420; 525/434; 525/397

(58) Field of Classification Search
USPC ................ 428/34.1; 525/420, 434, 397, 436; 525/537; 422/33, 23
See application file for complete search history.

(56) References Cited

U.S. PATENT DOCUMENTS

| | | |
|---|---|---|
| 3,803,085 A | 4/1974 | Takehoshi et al. |
| 3,847,867 A | 11/1974 | Heath et al. |
| 3,852,242 A | 12/1974 | White |
| 3,905,942 A | 9/1975 | Takekoshi et al. |
| 3,972,902 A | 8/1976 | Heath et al. |
| 3,983,093 A | 9/1976 | Williams, III et al. |
| 4,176,222 A | 11/1979 | Cinderey et al. |
| 4,293,670 A | 10/1981 | Robeson et al. |
| 4,443,591 A | 4/1984 | Schmidt et al. |
| 4,455,410 A * | 6/1984 | Giles, Jr. ....................... 525/436 |
| 4,473,684 A | 9/1984 | Maresca et al. |
| 4,503,168 A | 3/1985 | Hartsing, Jr. |
| 4,643,876 A | 2/1987 | Jacobs et al. |
| 5,037,902 A | 8/1991 | Harris et al. |
| 5,134,202 A | 7/1992 | Harris et al. |
| 5,212,259 A | 5/1993 | Harris et al. |
| 5,286,812 A | 2/1994 | Karasz et al. |
| 5,443,727 A * | 8/1995 | Gagnon ........................ 210/490 |
| 5,917,137 A | 6/1999 | Ekiner |
| 6,063,874 A | 5/2000 | Jin et al. |
| 6,077,480 A | 6/2000 | Edwards et al. |
| 6,482,880 B1 | 11/2002 | Rock |
| 7,041,773 B2 | 5/2006 | Gallucci et al. |
| 7,186,374 B2 | 3/2007 | Zelina et al. |
| 7,431,900 B2 | 10/2008 | Hill et al. |
| 7,902,316 B2 | 3/2011 | Johnson et al. |
| 2005/0113558 A1 | 5/2005 | Johnson et al. |
| 2006/0069236 A1 | 3/2006 | Brunelle et al. |
| 2007/0231201 A1 * | 10/2007 | Roberts et al. .................. 422/33 |
| 2007/0231202 A1 * | 10/2007 | Roberts et al. .................. 422/33 |
| 2009/0018242 A1 | 1/2009 | Kailasam et al. |
| 2010/0185270 A1 | 7/2010 | Ramzipoor et al. |
| 2010/0285084 A1 * | 11/2010 | Yang et al. ..................... 424/423 |
| 2012/0149094 A1 * | 6/2012 | Smith et al. ................ 435/288.7 |

FOREIGN PATENT DOCUMENTS

| | | |
|---|---|---|
| EP | 0207417 A1 | 1/1987 |
| EP | 0440433 A2 | 8/1991 |
| EP | 1270018 A1 | 1/2003 |
| EP | 1728828 A1 | 12/2006 |
| WO | 03090796 A1 | 11/2003 |
| WO | 2009009525 A1 | 1/2009 |
| WO | 2012015608 A1 | 2/2012 |

OTHER PUBLICATIONS

U.S. Appl. No. 13/486,435, filed with USPTO on Jun. 1, 2012.
U.S. Appl. No. 61/493,163, filed with USPTO on Jun. 3, 2011.
International Search Report for International Application No. PCT/US2008/069404; International Filing Date Jul. 8, 2008; Date of Mailing Nov. 6, 2008; 6 pages.
Written Opinion of the International Search Report for International Application No. PCT/US2008/069404; International Filing date Jul. 8, 2008; Date of Mailing Nov. 6, 2008; 5 pages.
International Search Report for International Application No. PCT/US2012/040443; International Filing Date Jun. 1, 2012; Date of Mailing Aug. 17, 2012; 5 pages.
Written Opinion of the International Search Report for Internaional Application No. PCT/US2012/040443; International Filing Date Jun. 1, 2012; Date of Mailing Aug. 17, 2012; 8 pages.
International Search Report for International Application No. PCT/US2012/040467; International Filing Date Jun. 1, 2012; Date of Mailing Sep. 4, 2012; 5 pages.
Written Opinion of the International Search Report for International Application No. PCT/US2012/040467; International Filing Date Jun. 1, 2012; Date of Mailing Sep. 4, 2012; 5 pages.

* cited by examiner

*Primary Examiner* — N. Edwards

(74) *Attorney, Agent, or Firm* — Cantor Colburn LLP; Diderico van Eyl

(57) ABSTRACT

A sterilized article comprising a hydrogen peroxide plasma or hydrogen peroxide vapor sterilized polymer composition, the polymer composition comprising from 20 to 80 weight % of a polyphenylene ether sulfone; and from 20 to 80 weight % of a polyetherimide. When sterilized with a hydrogen peroxide plasma, or hydrogen peroxide vapor, the articles have surprisingly improved resistance to changes in color and clarity as well as resistance to loss of mechanical properties.

31 Claims, No Drawings

STERILIZED POLYETHERIMIDE/POLYPHENYLENE ETHER SULFONE ARTICLES

CROSS REFERENCE TO RELATED APPLICATION

This application claims the benefit of U.S. Provisional Patent Application Ser. No. 61/493,140 filed Jun. 3, 2011, which is incorporated herein by reference in its entirety.

BACKGROUND

This disclosure relates to articles formed from polyetherimide/polyphenylene ether sulfone compositions.

Hydrogen peroxide plasma sterilization devices are known, such as described in U.S. Pat. No. 4,643,876. The article to be sterilized is placed in the plasma chamber, the chamber is closed, and vacuum is drawn on the chamber to remove the gas that is in the chamber. An aqueous solution of hydrogen peroxide is typically injected into the chamber, raising the pressure in the chamber to the desired level. The hydrogen peroxide remains in the chamber for a period of sufficient duration to allow the hydrogen peroxide to come in intimate contact with the item to be sterilized, before the plasma is generated at a power level sufficient to achieve sterilization. The power then remains on for the desired period to allow complete sterilization of the particular type of article being treated. As is known to those skilled in the art, the period of treatment will also vary depending upon the concentration of the hydrogen peroxide in the chamber and the amount of power that is applied to the chamber.

Hydrogen peroxide plasma sterilization devices are employed in health care facilities since they provide an easy and cost effective means of sterilizing healthcare devices prior to each use. Hydrogen peroxide plasma sterilization is an alternative to high temperature autoclave sterilization, especially for articles that include sensitive electronic or optical components that cannot be exposed to the high temperatures or moisture of an autoclave without becoming damaged. Hydrogen peroxide plasma sterilization systems operate at lower temperatures than high temperature autoclaves and in the absence of moisture to achieve sterilization of articles through the antimicrobial action of peroxide plasma instead of using extreme temperature. However, the adoption of hydrogen peroxide plasma sterilization has placed a new set of durability demands upon materials used to fabricate articles intended for repeated use in a sterile work environment, such as surgical devices of various types and configurations. Improvements in hydrogen peroxide plasma devices have increased the extent of diffusion of peroxide within the chamber, improving the ability to penetrate lumens and hinges, broadening the applicability of this technology to a wider range of instruments. In other instances a hydrogen peroxide vapor that may contain little or no hydrogen peroxide plasma may also be used for low temperature sterilization, for example as described in U.S. Pat. Nos. 7,431,900; 7,186,324, and 6,077,480, incorporated herein in their entirety.

Plastic components that are exposed to repeated hydrogen peroxide plasma sterilizations are thus subjected to repeated rigorous challenges from the action of hydrogen peroxide plasma, an ionized acidic vapor, upon the surface of the article and through diffusion below the surface of the article. Retention of properties after exposure to repeated cycles of peroxide plasma sterilization is therefore needed.

There accordingly remains a need in the art for improved sterilized plastic articles that will endure repeated exposures to peroxide plasma sterilization.

SUMMARY OF THE INVENTION

This disclosure relates to an article comprising a sterilized polymer composition, the polymer composition comprising from 20 to 80 weight % of a polyphenylene ether sulfone; and from 80 to 20 weight % of a polyetherimide, wherein after exposure to 100 cycles of the hydrogen peroxide plasma sterilization using a mixture of hydrogen peroxide vapor and hydrogen peroxide plasma for 30 minutes at 20 to 55° C., the color of polymer composition exhibits a color shift of delta E of 10 units or less relative to the color of the polymer composition before the first hydrogen peroxide plasma sterilization cycle, wherein delta E is measured in accordance with ASTM D2244.

In another embodiment, a sterilized article comprises a sterilized polymer composition, treated with a member selected from hydrogen peroxide plasma, hydrogen peroxide vapor, and combinations thereof, the polymer composition comprising a) from 20 to 80 weight % of a polyphenylene ether sulfone having a weight average molecular weight of 10,000 to 80,000 Daltons; and b) from 20 to 80 weight % of a polyetherimide having a weight average molecular weight of 10,000 to 80,000 Daltons.

In another embodiment, an article comprises the above hydrogen peroxide plasma-sterilized polymer composition, at least a portion of the polymer composition bearing an etched marking, wherein the etching is legible when observed from a distance of 0.3 meters without magnification after the exposure of the article to 100 cycles of the hydrogen peroxide plasma sterilization.

In another embodiment, in the sterilized article comprising a sterilized polymer composition, treated with a member selected from hydrogen peroxide plasma, hydrogen peroxide vapor, and combinations thereof, the polymer composition comprises a) from 80 to 20 weight % of a polyphenylene ether sulfone having a weight average molecular weight of 10,000 to 80,000 Daltons; the polyphenylene ether sulfone having the formula

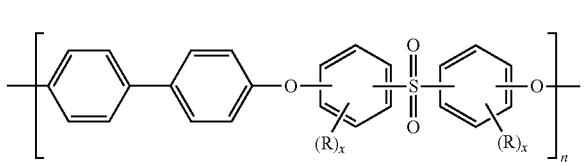

wherein
n is 25 to 1000,
R is selected from $C_{1-8}$ alkyl, aryl, alkyl aryl, alkoxy, halogen, and combinations thereof,
x is 0 to 4, and
the aryl sulfone linkages are selected from 4,4' linkages, 3,3' linkages, 3,4' linkages, and combinations thereof, and b) from 20 to 80 weight % of a polyetherimide having a weight average molecular weight of 10,000 to 80,000 Daltons;

wherein after exposure to 150 cycles of the hydrogen peroxide plasma sterilization using a mixture of hydrogen peroxide vapor and hydrogen peroxide plasma for 30 minutes at 20 to 55° C., the color of the polymer composition exhibits a color shift of delta E of 10 units or less relative to the color of the polymer composition before the first hydrogen peroxide plasma sterilization cycle, wherein delta E is measured in accordance with ASTM D2244-05 and an article molded from the composition (i) initially also exhibits a multiaxial impact energy of greater than or equal to 45 ft-lbs (61 Joules) and (ii) after 150 cycles hydrogen peroxide plasma exposure has a multiaxial impact energy of greater than or equal to 20 ft-lbs (27 Joules) and multiaxial impact energy is determined according to ASTM D5628-10 at 23° C.;

wherein at least a portion of the polymer composition has an etching, and wherein the etching is legible when observed from a distance of 0.3 meters without magnification after the exposure of the article to 100 cycles of hydrogen peroxide plasma sterilization.

In another embodiment, the above sterilized articles that are, or are components of, medical devices, surgical devices, sterilization devices, decontamination devices, food handling devices, food preparation devices, beverage handling devices, beverage preparation devices, and combinations thereof.

DETAILED DESCRIPTION

The present inventors have discovered that peroxide plasma-sterilized articles comprising polyetherimide/polyphenylene ether sulfone blend have surprising and important features. Surprisingly, it has been discovered that peroxide plasma-sterilized articles retain their original appearance better than articles of polyphenylene ether sulfone without polyetherimide. Remarkably, the peroxide plasma-sterilized articles can also retain advantageous multiaxial impact energies as well as tensile strength and elongation after being exposed to numerous sterilization cycles.

In particular, such polyetherimide/polyphenylene ether sulfone articles exhibit better color retention, superior retention of mechanical properties, and retain etched surface markings better than articles molded from polyphenylene ether sulfone. These performance advantages allow peroxide plasma-sterilized articles molded from polyetherimide/polyphenylene ether sulfone blend to remain in service through more cycles of peroxide plasma or peroxide vapor sterilization and used in sterile work environments longer than articles molded from polyphenylene ether sulfone (PPSU).

Various numerical ranges are disclosed in this patent application. Because these ranges are continuous, they include every value between the minimum and maximum values. Unless expressly indicated otherwise, the various numerical ranges specified in this application are approximations. The endpoints of all ranges directed to the same component or property are inclusive of the endpoint and independently combinable.

The terms "a" and "an" do not denote a limitation of quantity, but rather denote the presence of at least one of the referenced item. "Or" means "and/or." As used herein, "combination thereof" is inclusive of one or more of the recited elements, optionally together with a like element not recited. Reference throughout the specification to "an embodiment," "another embodiment," "some embodiments," and so forth, means that a particular element (e.g., feature, structure, property, and/or characteristic) described in connection with the embodiment is included in at least an embodiment described herein, and may or may not be present in other embodiments. In addition, it is to be understood that the described element(s) can be combined in any suitable manner in the various embodiments.

All molecular weights in this application refer to weight average molecular weights (Mw) unless indicated otherwise. All such mentioned molecular weights are expressed in Daltons.

Compounds are described using standard nomenclature. For example, any position not substituted by any indicated group is understood to have its valency filled by a bond as indicated, or a hydrogen atom. A dash ("-") that is not between two letters or symbols is used to indicate a point of attachment for a substituent. For example, —CHO is attached through carbon of the carbonyl group. The term "alkyl" includes both $C_{1-30}$ branched and straight chain, unsaturated aliphatic hydrocarbon groups having the specified number of carbon atoms. Examples of alkyl include, but are not limited to, methyl, ethyl, n-propyl, i-propyl, n-butyl, s-butyl, t-butyl, n-pentyl, s-pentyl, n- and s-hexyl, n- and s-heptyl, and, n- and s-octyl. The term "aryl" means an aromatic moiety containing the specified number of carbon atoms, such as to phenyl, tropone, indanyl, or naphthyl.

All ASTM tests are based on the 2003 edition of the Annual Book of ASTM Standards unless otherwise indicated.

Polyetherimides can comprise more than 1, for example 10 to 1000, or, more specifically, 10 to 500 structural units, of the formula (1)

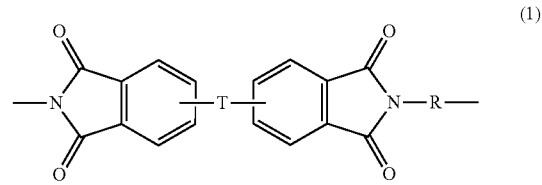

wherein R can be, for example substituted or unsubstituted divalent organic groups such as: (a) aromatic hydrocarbon groups having 6 to 24 carbon atoms and halogenated derivatives thereof; (b) straight or branched chain alkylene groups having 2 to 20 carbon atoms; (c) cycloalkylene groups having 3 to 24 carbon atoms, or (d) divalent groups of formula (2)

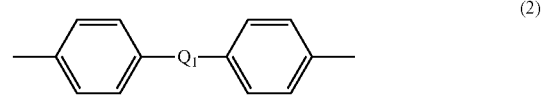

wherein $Q^1$ is selected from —O—, —S—, —C(O)—, —$SO_2$—, —SO—, and —$C_yH_{2y}$— and fluorinated derivatives thereof wherein y is an integer from 1 to 5. Examples of groups R include divalent groups of the following formulae (A)

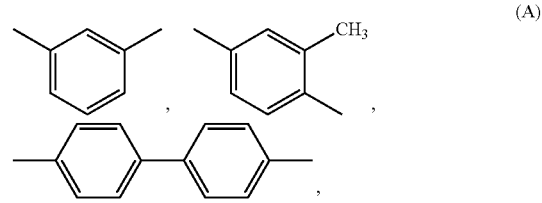

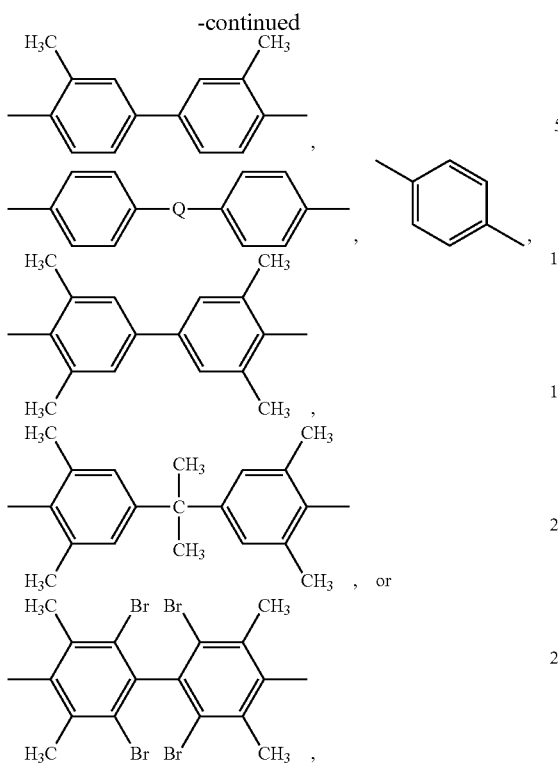

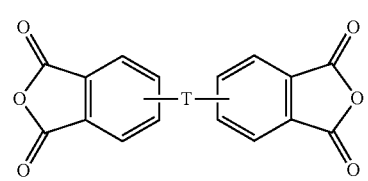

or combinations thereof, wherein Q is a divalent moiety selected from —O—, —C(O)—, —S—, $C_yH_{2y}$— (y being an integer from 1 to 5), and fluorinated derivatives thereof, including perfluoroalkylene groups. In a specific embodiment Q selected from —O—, —C(O)—, $C_yH_{2y}$— (y being an integer from 1 to 5), and fluorinated derivatives thereof, including perfluoroalkylene groups.

Further in formula (1), T is —O— or a group of the formula —O—Z—O— wherein the divalent bonds of the —O— or the —O—Z—O— group are in the 3,3', 3,4', 4,3', or the 4,4' positions. Z includes, but is not limited to, substituted or unsubstituted divalent organic groups such as: (a) aromatic hydrocarbon groups having about 6 to about 20 carbon atoms and halogenated derivatives thereof; (b) straight or branched chain alkylene groups having about 2 to about 20 carbon atoms; (c) cycloalkylene groups having about 3 to about 20 carbon atoms, or (d) divalent groups of formula (3)

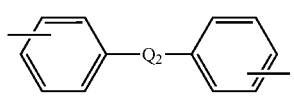

(3)

wherein $Q^2$ includes but is not limited to a divalent moiety selected from —O—, —C(O)—, —S—, $C_yH_{2y}$— (y being an integer from 1 to 5), and fluorinated derivatives thereof, including perfluoroalkylene groups. In a specific embodiment Q selected from —O—, —C(O)—, —$C_yH_{2y}$— (y being an integer from 1 to 5), and fluorinated derivatives thereof, including perfluoroalkylene groups.

In a specific embodiment the polyetherimide is a polymer of formula (1) wherein T is a group of the formula —O—Z—O— as described above. More specifically in Formula (1), R is a group of formula (A), specifically m-phenylene or p-phenylene, and Z is a group of formula (3), specifically a group derived from bisphenol A. In some embodiments, the polyetherimide can be a copolymer. Combinations of polyetherimides can also be used.

The polyetherimide can be prepared by any of the methods well known to those skilled in the art, including the reaction of an aromatic bis(ether anhydride) of the formula (4)

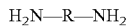

(4)

with an organic diamine of the formula (5)

$$H_2N—R—NH_2 \quad (5)$$

wherein T and R are defined as described above.

Examples of specific aromatic bis(ether anhydride)s and organic diamines are disclosed, for example, in U.S. Pat. Nos. 3,972,902 and 4,455,410. Illustrative examples of aromatic bis anhydrides include: 3,3-bis[4-(3,4-dicarboxyphenoxy)phenyl]propane dianhydride; 4,4'-bis(3,4-dicarboxyphenoxy)diphenyl ether dianhydride; 4,4'-bis(3,4-dicarboxyphenoxy)diphenyl sulfide dianhydride; 4,4'-bis(3,4-dicarboxyphenoxy)benzophenone dianhydride; 4,4'-bis(3,4-dicarboxyphenoxy)diphenyl sulfone dianhydride; 2,2-bis[4-(2,3-dicarboxyphenoxy)phenyl]propane dianhydride; 4,4'-bis(2,3-dicarboxyphenoxy)diphenyl ether dianhydride; 4,4'-bis(2,3-dicarboxyphenoxy)diphenyl sulfide dianhydride; 4,4'-bis(2,3-dicarboxyphenoxy)benzophenone dianhydride; 4,4'-bis(2,3-dicarboxyphenoxy)diphenyl sulfone dianhydride; 4-(2,3-dicarboxyphenoxy)-4'-(3,4-dicarboxyphenoxy)diphenyl-2,2-propane dianhydride; 4-(2,3-dicarboxyphenoxy)-4'-(3,4-dicarboxyphenoxy)diphenyl ether dianhydride; 4-(2,3-dicarboxyphenoxy)-4'-(3,4-dicarboxyphenoxy)diphenyl sulfide dianhydride; 4-(2,3-dicarboxyphenoxy)-4'-(3,4-dicarboxyphenoxy)benzophenone dianhydride; and, 4-(2,3-dicarboxyphenoxy)-4'-(3,4-dicarboxyphenoxy)diphenyl sulfone dianhydride, as well as various combinations thereof. Another class of aromatic bis (ether anhydride)s included in formula (4) above includes compounds wherein T is of the formula (6)

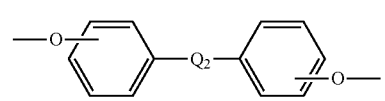

(6)

wherein the ether linkages are in the 4,4', 3,3', 3,4', or 4,3' positions, specifically the 4,4' positions, and Q is as defined above.

Examples of organic diamines include ethylenediamine, propylenediamine, trimethylenediamine, diethylenetriamine, triethylene tetramine, hexamethylenediamine, heptamethylenediamine, octamethylenediamine, nonamethylenediamine, decamethylenediamine, 1,12-dodecanediamine, 1,18-octadecanediamine, 3-methylheptamethylenediamine, 4,4-dimethylheptamethylenediamine, 4-methylnonamethylenediamine, 5-methylnonamethylenediamine, 2,5-dimethylhexamethylenediamine, 2,5-dimethylheptamethylenediamine, 2,2-dimethylpropylenediamine, N-methyl-bis(3-aminopropyl)amine, 3-methoxyhexamethylenediamine, 1,2- bis(3-aminopropoxy)ethane, bis(3-aminopropyl)sulfide, 1,4-cyclohexanediamine, bis-(4-aminocyclohexyl)methane, m-phenylenediamine, p-phenylenediamine, 2,4-diaminotoluene, 2,6-diaminotoluene, m-xylylenediamine, p-xylylenediamine, 2-methyl-4,6-diethyl-1,3-phenylene-diamine, 5-methyl-4,6-diethyl-1,3-phenylene-diamine, benzidine, 3,3'-dimethylbenzidine, 3,3'-dimethoxybenzidine, 1,5-diaminonaphthalene, bis(4-aminophenyl)methane, bis(2-chloro-4-amino-3,5-diethylphenyl)methane, bis(4-aminophenyl)propane, 2,4-bis(p-amino-t-butyl)toluene, bis(p-amino-t-butylphenyl)ether, bis(p-methyl-o-aminophenyl)benzene, bis(p-methyl-o-aminopentyl)benzene, 1,3-diamino-4-isopropylbenzene, bis(4-aminophenyl)sulfide, bis-(4-aminophenyl)sulfone, and bis(4-aminophenyl)ether. Combinations of these compounds can also be used. In some embodiments the organic diamine comprises m-phenylenediamine, p-phenylenediamine, sulfonyl dianiline, or combinations thereof.

In an embodiment, the polyetherimide polymer comprises structural units according to formula (1) wherein each R is independently p-phenylene, m-phenylene or a combination thereof and T is a divalent group of the formula (7)

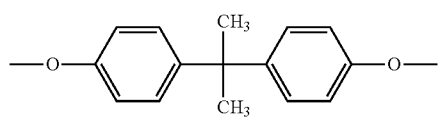

(7)

In this embodiment, the polyetherimide can have less than 5 ppm of free bisphenol A.

Included among the many methods of making polyetherimides are those disclosed in U.S. Pat. Nos. 3,847,867, 3,852,242, 3,803,085, 3,905,942, 3,983,093, 4,443,591 and 7,041,773. These patents mentioned for the purpose of teaching, by way of illustration, general and specific methods for preparing polyimides. Some polyetherimide (PEI) materials are described in ASTM D5205-96 Standard Classification System for Polyetherimide Materials.

Polyetherimides can have a melt index of 0.1 to 10 grams per minute (g/min), as measured by American Society for Testing Materials (ASTM) D1238 at 340 to 370° C., using a 6.7 kilogram (kg) weight. In some embodiments, the polyetherimide polymer has a weight average molecular weight (Mw) of 1,000 to 150,000 grams/mole (Dalton), as measured by gel permeation chromatography, using polystyrene standards. In some embodiments the polyetherimide has Mw of 10,000 to 80,000 Daltons. Such polyetherimide polymers typically have an intrinsic viscosity greater than 0.2 deciliters per gram (dl/g), or, more specifically, 0.35 to 0.7 dl/g as measured in m-cresol at 25° C.

In an embodiment, the polyetherimide comprises less than 50 ppm amine end groups. In other instances the polymer will have less than 5 ppm of free, unpolymerized bisphenol A (BPA).

The polyetherimide is present in an amount of 20 to 80 weight percent, based on the combined weight of polyetherimide and polyphenylene ether sulfone. Within this range the polyetherimide can be present in an amount from about 30 to 75 weight percent, or, more specifically, from about 30 to 60 weight percent. Also within this range the polyetherimide can be present in an amount from about 30 to 70 weight percent. Additionally, within this range the polyetherimide can be present in an amount from about 40 to about 60 weight percent.

Polyphenylene ether sulfones comprise repeating units having both an ether linkage and an aryl sulfone linkage in the backbone of the polymer as shown in formula (8)

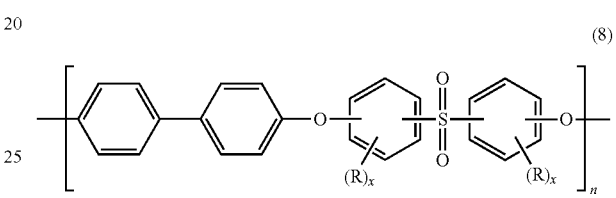

(8)

wherein R is hydrogen, alkyl, aryl, alkyl aryl, alkoxy, halogen or combinations thereof, each x equals 0 to 4, more specifically 0, and n equals 25 to 1000, or, more specifically, n equals 25 to 500, or, more specifically, n equals 25 to 100. The aryl sulfone linkages can be 4,4', 3,3', 3,4' or combinations thereof. In some embodiments the aryl sulfone linkages are 4,4' diaryl sulfone. In some embodiments greater than or equal to 50 mole percent of the main chain sulfone linkages are derived from biphenol.

An exemplary biphenol polyphenylene ether sulfone (PPSU) is shown in formula (9)

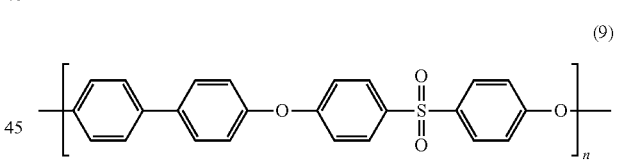

(9)

wherein n is as defined above.

In some embodiments, the polyphenylene ether sulfone is a polyphenylene ether sulfone copolymer of formula (10)

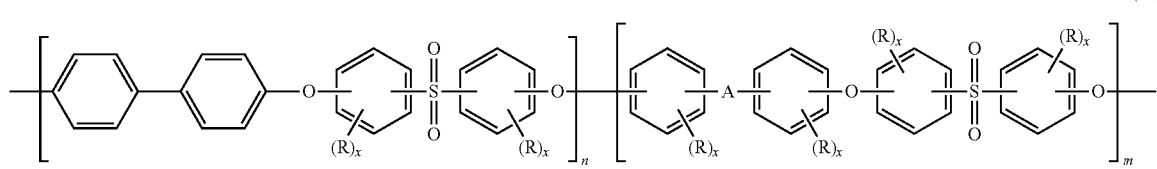

(10)

wherein A is a linking group selected from, —O—, —S—, —SO$_2$—, C$_6$-C$_{18}$ aryl, and C$_3$-C$_{12}$ alkyl. In some embodiments A is isopropylidene. Linkages of A to the aryl groups can be at the 4,4', 3,3', 3,4' positions or combinations thereof. In many embodiments the linkages are at the 4,4' positions.

Aryl sulfone linkages can be at the 4,4', 3,3', 3,4' positions or combinations thereof. In many embodiments the linkages are at the 4,4' positions. R and x are defined as above; n>m, n+m=20 to 1000, or, more specifically, n+m=25 to 500, or, even more specifically, n+m=25 to 100. In some embodiments the polyphenylene ether sulfones have n equal to 70% and m equal to 30% based on the total of n+m. In some embodiments n equals 80% and m equals 20%, based on the total of n+m. In an embodiment, m=0 in polymer (10). When m=0, the polyphenylene ether sulfone is a homopolymer.

Exemplary aromatic dihydroxy compounds that can be used to make the polyphenylene ether sulfone copolymers include bisphenols and biphenols such as bisphenol A, dimethyl cyclohexyl bisphenol, dihydroxy diphenyl ether, hydroquinone, methyl hydroquinone and 4,4'-biphenol. Other exemplary aromatic dihydroxy compounds are disclosed in United States Patent Publication Nos. 2006/0167216, 2005/0113558, and 2006/0069236.

The polyphenylene ether sulfone can be a homopolymer, copolymer, or a combination thereof, or a combination of different polyphenylene ether sulfones. Copolymers include random copolymers, non-random copolymers and block copolymers.

An example of a polyphenylene ether sulfone copolymer is shown below in formula (11)

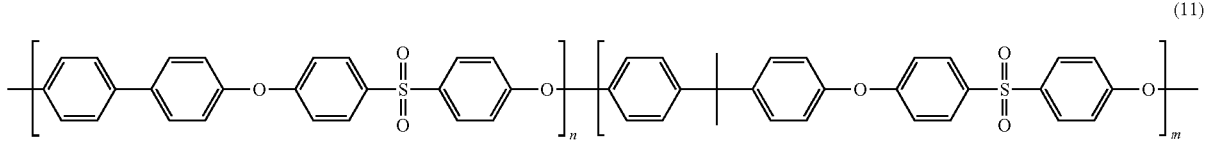

(11)

wherein n>m, n+m=25 to 100, A (from formula (10)) is isopropyl, all aryl linkages are at the 4,4' positions and R (from formula (10)) is hydrogen.

Polyphenylene ether sulfones are commercially available, including the polycondensation product of biphenol with dichloro diphenyl sulfone. Methods for the preparation of polyphenylene ether sulfones are widely known and several suitable processes have been well described in the art. Two methods, the carbonate method and the alkali metal hydroxide method, are known to the skilled artisan. In the alkali metal hydroxide method, a double alkali metal salt of a dihydric phenol is contacted with a dihalobenzenoid compound in the presence of a dipolar, aprotic solvent under substantially anhydrous conditions. The carbonate method, in which a dihydric phenol and a dihalobenzenoid compound are heated, for example, with sodium carbonate or bicarbonate and a second alkali metal carbonate or bicarbonate is also disclosed in the art, for example in U.S. Pat. No. 4,176,222. Alternatively, the polyphenylene ether sulfone can be prepared by any of the variety of methods known in the art including those described in the United States Patent Publications referenced above.

The molecular weight of the polyphenylene ether sulfone, as indicated by reduced viscosity data in an appropriate solvent such as methylene chloride, chloroform, N-methylpyrrolidone, or the like, can be greater than or equal to 0.3 dl/g, or, more specifically, greater than or equal to 0.4 dl/g and, typically, will not exceed 1.5 dl/g.

The polyphenylene ether sulfone weight average molecular weight (Mw) can be 10,000 to 100,000 Daltons as determined by gel permeation chromatography using ASTM D5296 with polystyrene standards. In some embodiments the polyphenylene ether sulfone weight average molecular weight can be 10,000 to 80,000 Daltons. Polyphenylene ether sulfones can have glass transition temperatures (Tg) of 180 to 250° C.

In some embodiments the polyphenylene ether sulfone has less than 50 ppm hydroxyl groups, and the polyphenylene ether sulfone is methyl ether end-capped.

The polyphenylene ether sulfone is present in an amount of 20 to 80 weight percent, based on the combined weight of polyetherimide and polyphenylene ether sulfone. Within this range the polyphenylene ether sulfone can be present in an amount from about 30 to 75 weight percent or from about 40 to 70 weight percent. Also within this range the polyphenylene ether sulfone can be present in an amount from about 30 to 70 weight percent. Additionally, within this range the polyphenylene ether sulfone can be present in an amount from about 40 to about 60 weight percent.

The polyetherimides and polyphenylene ether sulfones can have low levels of residual volatile species, such as residual solvent. In some embodiments, the polyetherimide and the polyphenylene ether sulfone each have a residual volatile species concentration of less than 1000 parts by weight per million parts by weight (ppm), or, more specifically, less than 500 ppm, or, more specifically, less than 300 ppm, or, even more specifically, less than 100 ppm. In some embodiments, the polyetherimide/polyphenylene ether sulfone composition has a residual volatile species concentration of less than 1000 parts by weight per million parts by weight (ppm), or, more specifically, less than 500 ppm, or, more specifically, less than 300 ppm, or, even more specifically, less than 100 ppm.

Examples of residual volatile species are halogenated aromatic compounds such as chlorobenzene, dichlorobenzene, trichlorobenzene, aprotic polar solvents such as dimethyl formamide (DMF), N-methylpyrrolidinone (NMP), dimethyl sulfoxide (DMSO), diaryl sulfones, sulfolane, pyridine, phenol, veratrole, anisole, cresols, xylenols, dichloro ethanes, tetra chloro ethanes, pyridine, and combinations thereof.

Low levels of residual volatile species in the final polymer product can be achieved by known methods, for example, by devolatilization or distillation. In some embodiments the bulk of any solvent can be removed and any residual volatile species can be removed from the polymer product by devolatilization or distillation, optionally at reduced pressure. In other embodiments the polymerization reaction is taken to some desired level of completion in solvent and then the polymerization is essentially completed and most remaining water is removed during at least one devolatilization step following the initial reaction in solution. Apparatuses to devolatilize the polymer mixture and reduce solvent and other volatile species to the low levels needed for good melt processability are generally capable of high temperature heating under vacuum with the ability to rapidly generate high surface area to facilitate removal of the volatile species. The mixing portions of such apparatuses are generally capable of supplying sufficient power to pump, agitate, and stir the high temperature, amorphous polyphenylene ether sulfone and polyetherimide melt which can be very viscous. Suitable devolatilization apparatuses include, but are not limited to, wiped films evaporators, for example those made by the LUWA Company and devolatilizing extruders, especially twin screw extruders with multiple venting sections, for example those made by the Coperion Company or Welding Engineers.

In some compositions the polyetherimide and the polyphenylene ether sulfone each have a weight average molecular weight of 10,000 to 80,000 Daltons, specifically 20,000 to 70,000 Daltons, where the difference in molecular weight between the two polymers is less than 20% of the higher of the molecular weights. In some embodiments the difference in molecular weight between the two polymers is less than 10% of the higher of the molecular weights. Having a large difference in Mw between the polyetherimide and polyphenylene ether sulfone polymer components can cause problems during melt blending and extrusion, e.g., surging and die swell that prevent efficient compounding and pelletization of the compositions. Melt processing is facilitated by having a small, e.g., less than 20%, molecular weight difference between the polymers.

In some embodiments the polyetherimide has a glass transition temperature of 200 to 280° C. and the polyphenylene ether sulfone has a glass transition temperature of 200 to 250° C.

It is often useful to melt filter the polyetherimide and polyphenylene ether sulfone using known melt filtering techniques to remove foreign material, carbonized particles, cross-linked polymer, or similar impurities. Melt filtering can occur during initial polymer isolation or in a subsequent step. The polyetherimide/polyphenylene ether sulfone compositions can be melt filtered in the same extrusion operation where they are blended together. Melt filtering can be performed using a filter with pore size sufficient to remove particles with a dimension of greater than or equal to 100 micrometers or with a pore size sufficient to remove particles with a dimension of greater than or equal to 40 micrometers.

The polyetherimide/polyphenylene ether sulfone compositions can optionally comprise additives such as UV absorbers; stabilizers such as light stabilizers and others; lubricants; plasticizers; pigments; dyes; colorants; anti-static agents; metal deactivators; and combinations comprising one or more of the foregoing additives. In some embodiments, the additive can include a combination of a mold release agent and a stabilizer selected from phosphite stabilizers, phosphonite stabilizers, hindered phenol stabilizers, and combinations thereof. In an embodiment, a phosphorus-containing stabilizer is used.

The polyetherimide/polyphenylene ether sulfone composition may include fillers or reinforcing agents Where used, useful fillers or reinforcing agents include, for example, silicates and silica powders such as aluminum silicate (mullite), synthetic calcium silicate, zirconium silicate, fused silica, crystalline silica graphite, natural silica sand, or the like; boron powders such as boron-nitride powder, boron-silicate powders, or the like; oxides such as $TiO_2$, aluminum oxide, magnesium oxide, or the like; calcium sulfate; calcium carbonates such as chalk, limestone, marble, synthetic precipitated calcium carbonates, or the like; talc, including fibrous, modular, needle shaped, lamellar talc, or the like; wollastonite; surface-treated wollastonite; glass spheres such as hollow and solid glass spheres, silicate spheres, cenospheres, aluminosilicate (armospheres), or the like; kaolin, including hard kaolin, soft kaolin, calcined kaolin, kaolin comprising various coatings known in the art to facilitate compatibility with the polymeric matrix resin, or the like; single crystal fibers or "whiskers" such as silicon carbide, alumina, boron carbide, iron, nickel, copper, or the like; fibers (including continuous and chopped fibers) such as carbon fibers, glass fibers, such as E, A, C, ECR, R, S, D, or NE glasses, or the like; sulfides such as molybdenum sulfide, zinc sulfide or the like; barium compounds such as barium titanate, barium ferrite, barium sulfate, heavy spar, or the like; metals and metal oxides such as particulate, flake or fibrous aluminum, bronze, zinc, copper and nickel or the like; flaked fillers such as glass flakes, flaked silicon carbide, aluminum diboride, aluminum flakes, steel flakes or the like; fibrous fillers, for example short inorganic fibers such as those derived from blends comprising at least one of aluminum silicates, aluminum oxides, magnesium oxides, and calcium sulfate or the like; organic fillers such as polytetrafluoroethylene; reinforcing organic fibrous fillers formed from organic polymers capable of forming fibers such as polyimide, polybenzoxazole, aromatic polyimides, polytetrafluoroethylene or the like; as well as additional fillers and reinforcing agents such as mica, clay, feldspar, flue dust, fillite, quartz, quartzite, perlite, tripoli, diatomaceous earth, carbon black, or the like, or combinations comprising at least one of the foregoing fillers or reinforcing agents. The fillers and reinforcing agents may be in the form of nanoparticles, that is, particles with a median particle size ($D_{50}$) smaller than 100 nanometers as determined using light scattering methods.

Antioxidants can be compounds such as phosphites, phosphonites, hindered phenols, or combinations thereof. Phosphorus-containing stabilizers including triaryl phosphites and aryl phosphonates are of note as useful additives. Difunctional phosphorus containing compounds can also be employed. In some embodiments, to prevent loss of the stabilizer during melt mixing or subsequent melt forming processes such as injection molding, the phosphorus containing stabilizers with a molecular weight greater than or equal to 300 Dalton, but less than or equal to 5,000 Dalton, are useful. The additive can comprise hindered phenols with molecular weight over 500 Dalton. Phosphorus-containing stabilizers can be present in the composition at 0.01 to 3.0% or to 1.0% by weight of the total composition.

The polyetherimide/polyphenylene ether sulfone compositions can optionally comprise a mold-release agent. Examples of the mold-release agents include, but are not limited to, natural and synthetic paraffins, polyethylene waxes, fluorocarbons, and other hydrocarbon mold-release agents, stearic acid and other higher fatty acids, stearic acid amide, ethylene bis stearamide, and other fatty acid amides, alkylene bis fatty acid amides, and other fatty acid amide mold-release agents, stearyl stearate, pentaerythritol tetrastearate, and other alcohol esters of fatty acid, polyhydric alcohol esters of fatty acid, and other fatty acid ester mold release agents, silicone oil and other silicone mold release agents, and combinations of any of the aforementioned. In some embodiments at least 0.5 weight percent, for example 0.05 to 5.0 weight percent, based on the total weight of the composition, of a mold release agent selected from $C_6$ to $C_{36}$ alkyl carboxylic esters, $C_6$ to $C_{36}$ alkyl carboxylic acids, $C_6$ to $C_{36}$ alkyl carboxylic acid salts, $C_6$ to $C_{36}$ aliphatic carboxylic amides, polyolefins, and combinations thereof are used.

A wide variety of colorants can be used, including dyes and pigments. For example, the polyetherimide/polyphenylene ether sulfone compositions can comprise from 0.1 to 10.0 weight percent of a colorant, for example a pigment such as pigments selected from rutile titanium dioxide, anatase titanium dioxide, coated titanium dioxide, passivated titanium dioxide, and encapsulated titanium dioxide. The titanium dioxide can have a particle size of from 0.1 to 10 micrometers. In some instances the pigment can also be carbon black, (for example pigment black 7), solvent red 52, solvent violet 36, solvent violet 13, pigment brown 24, pigment blue 29, pigment blue 15:4 or combinations thereof.

The composition may also contain a biocidal additive component, in particular antimicrobial additive component. Biocides for use in polymer compositions include metals, for example copper, silver, zinc, or combinations thereof, inorganic compounds such as silanes, and various organic compounds, which can be any of those known in the art, for example chlorinated phenols such as 5-chloro-2-(2,4-dichlorophenoxy)phenol), polyhexamethylene biguanide hydrochloride (PHMB), doxycycline, chlorhexidine, metronidazole, thymol, enalypol, methyl salicylate, and the like. Biocides as used herein include those classified as germicides, antimicrobials, antibiotics, antibacterials, antivirals, antifungals, antiprotozoals, antiyeast, antialgae, and antiparasites. Combinations of different biocides can be used, for example a combination of microparticulate or nanoparticulate silver or silver containing compound (e.g., silver sulfate, silver zeolites, and silver functionalized clay) and a zinc oxide. The biocide is used in an amount effective to provide the desired activity, for example an amount from more than 0 to 5 weight percent of the total polymer composition. In some instances the biocide will be thermally stable at the polymer processing temperature of 300° C. or greater. Inorganic biocides are preferred.

The polyetherimide/polyphenylene ether sulfone compositions can also comprise other polymers such as polysulfones, polyethersulfones, silicone polyetherimides, polyamides, polyphenylene ethers, polyolefins, and combinations thereof, provided that they are used in such amount as not to compromise the multiaxial impact energy, tensile modulus, and heat distortion temperature or color stability properties enumerated herein. In some embodiments such polymers can be added to the composition in amounts of 1 to 40 weight percent, or 1 to 30 weight percent, or 1 to 20 weight percent, based on the total weight of the composition. In an embodiment, no other polymer is present. In these embodiments, the compositions comprise from 20 to 80 weight % of the polyphenylene ether sulfone and from 80 to 20 weight % of the polyetherimide; from 30 to 70 weight % of the polyphenylene ether sulfone and from 70 to 30 weight % of the polyetherimide; or from 40 to 60 weight % of the polyphenylene ether sulfone and from 60 to 40 weight % of the polyetherimide.

The polyetherimide/polyphenylene ether sulfone compositions can be prepared by melt mixing or a combination of dry blending and melt mixing. Melt mixing can be performed in single or twin screw type extruders or similar mixing devices that can apply a shear and heat to the components. Melt mixing can be performed at temperatures greater than or equal to the melting temperatures of the polyetherimide and polyphenylene ether sulfone and less than the degradation temperatures of any of the components of the composition. In some embodiments suitable melt mixing is achieved at a temperature of 125 to 150° C. above the highest glass transition temperature of the two polymers. All of the ingredients can be added initially to the processing system. In some embodiments, the ingredients can be added sequentially or through the use of one or more master batches.

The polyetherimide/polyphenylene ether sulfone compositions can be used to make articles (including portions of articles). Articles can be made by any suitable method, e.g., injection molding, compression molding, sintering, thermoforming, blow molding, profile extrusion, film extrusion, melt spinning, gas assist molding, foam molding, rotomolding, solvent casting, and the like. Articles can also comprise non-plastic parts such as metal and ceramic components for example screws, fasteners, inserts, blades, conductors, antennas, coatings and etc.

The articles can have a number of advantageous properties, in particular color stability. For example, after exposure to 100 cycles of hydrogen peroxide plasma sterilization using a mixture of hydrogen peroxide vapor and hydrogen peroxide plasma for 15 minutes at 20 to 55° C., the color of the polymer composition of the article (for simplicity, "the article") can exhibit a color shift delta E of 10 units or less, or 5 units or less, relative to the color of the article color before the first hydrogen peroxide plasma sterilization cycle, wherein delta E is measured in accordance with ASTM D2244. For example, after exposure to 300 cycles of hydrogen peroxide plasma sterilization using a mixture of hydrogen peroxide vapor and hydrogen peroxide plasma for 15 minutes from 20 to 55° C., the color of the article can exhibit a delta E of 0.5 to 10 units, 0.5 to 8 units, 0.5 to 6 units, 0.5 to 5 units, 0.5 to 4 units, or 0.5 to 2 units, relative to the color of the article color before the first hydrogen peroxide plasma sterilization cycle, wherein delta E is measured in accordance with ASTM D2244.

In another embodiment, the delta E of the article is 10 units or less or 5 units or less after exposure of the article to 100 to 300 sterilization cycles, wherein each cycle is from 10 to 60 minutes and from 20 to 55° C. For example, after exposure to 100 to 200 cycles of hydrogen peroxide plasma sterilization using a mixture of hydrogen peroxide vapor and hydrogen peroxide plasma for 10 to 60 minutes from 20 to 55° C., the color of the article can exhibit a delta E of 0.5 to 10 units, 0.5 to 8 units, 0.5 to 6 units, 0.5 to 5 units, 0.5 to 4 units, or 0.5 to 2 units, relative to the color of the article color before the first hydrogen peroxide plasma sterilization cycle, wherein delta E is measured in accordance with ASTM D2244.

In still another embodiment, the delta E of an article comprising the polyetherimide/polyphenylene ether sulfone compositions is less than a delta E of another article comprising the same polymer composition without the polyetherimide, wherein each delta E is measured after exposure to 100 cycles of hydrogen peroxide plasma sterilization under the same conditions, for example 100 to 200 sterilization cycles, wherein each cycle is from 10 to 60 minutes at 20 to 55° C.

In a further embodiment, an article (i) initially exhibits a multiaxial impact energy of greater than or equal to 45 ft-lbs (61 Joules) and (ii) after 150 cycles hydrogen peroxide plasma exposure has a multiaxial impact energy of greater than or equal to 20 ft-lbs (27 Joules) where multiaxial impact energy is determined according to ASTM D5628-10 at 23° C.

In an additional embodiment, after exposure to 100 cycles of hydrogen peroxide plasma sterilization using a mixture of hydrogen peroxide vapor and hydrogen peroxide plasma for 15 minutes at 20 to 55° C., the color of the article exhibits a color shift of delta E of 10 units or less relative to the color of the article color before the first hydrogen peroxide plasma sterilization cycle, wherein delta E is measured in accordance with ASTM D2244 and an article molded from the composition (i) initially also exhibits a multiaxial impact energy of greater than or equal to 45 ft-lbs (61 Joules) and (ii) after 300 cycles hydrogen peroxide plasma exposure has a multiaxial impact energy of greater than or equal to 20 ft-lbs (27 Joules) where multiaxial impact energy is determined according to ASTM D3763 at 23° C.

The articles further resist surface erosion/abrasion during hydrogen peroxide plasma sterilization. In particular, the articles can have an etching on at least a portion of the surface of the polymer composition (for example for identification purposes). In some embodiments the etching is legible when observed from a distance of 0.3 meters without magnification after the exposure of the article to 100 cycles of hydrogen peroxide plasma sterilization under a variety of conditions, for example after exposure of the article to 100 to 200 sterilization cycles, wherein each cycle is from 10 to 60 minutes at 20 to 55° C. The articles' capacity to further resist surface abrasion with hydrogen peroxide plasma sterilization can also be evidenced by the capacity of the articles to retain their respective mass. In an embodiment, an article can retain at least 90% of its initial mass after the article has been exposed to 100 cycles of hydrogen peroxide plasma sterilization under a variety of conditions. In an embodiment, an article can retain at least 91%, 92%, 93%, 94%, 95%, 96%, 97%, 98%, 99%, 99.9% of its initial mass after the article has been exposed to 100 cycles of hydrogen peroxide plasma sterilization under a variety of conditions. Exemplary conditions include each cycle being from 10 to 60 minutes at 20 to 55° C., such as 15 minutes at 20 to 55° C.

Exemplary articles comprising the polyetherimide/polyphenylene ether sulfone composition include molded parts, sheets, slabs, profiles, films, or fibers. The articles can also include devices and components of devices such as medical devices, dental devices, sterilization devices, surgical devices, water purification devices, decontamination devices, and food and/or preparation and/or handling devices, such as part of a device or system for collecting, transporting, or handling beer, wine, milk, cheese, or other dairy products. Specific items include surgical instrument trays, handles, animal cages, bottles, cups, syringe bodies, endoscopes, ureteroscopes, catheters, clamps, cables, telescopes, forceps, scissors, drills, and the like.

Additional articles include and are not limited to, stereo tactic equipment, defibrillator paddles, electrocautery instruments, esophageal dilators, laryngoscope blades, cryoprobes, dopplers, endoscopic instruments, fiberoptic light cables, laser hand pieces, fibers, and accessories, rigid and flexible endoscopes, cranial pressure transducer cables, trocar sheaths, video cameras and couplers, pigmentation hand pieces, resectoscope/working elements and sheaths, shaver hand pieces, surgical power equipment and batteries, ultrasound probes, ophthalmic lenses, patient lead cables, instrument tray mats, forceps, scissors, medical keyboard and mice, medical bags and pouches, and the like.

At least the following Embodiments are encompassed by the foregoing description.

Embodiment 1

A sterilized article comprising a sterilized polymer composition, treated with a member selected from hydrogen peroxide plasma, hydrogen peroxide vapor, and combinations thereof, the polymer composition comprising
a) from 80 to 20 weight % of a polyphenylene ether sulfone having a weight average molecular weight of 10,000 to 80,000 Daltons; the polyphenylene ether sulfone having the formula

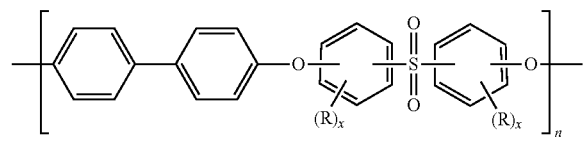

wherein n is 25 to 1000, R is selected from $C_{1-8}$ alkyl, aryl, alkyl aryl, alkoxy, halogen, and combinations thereof; x is 0 to 4 and the aryl sulfone linkages are selected from 4,4' linkages, 3,3' linkages, 3,4' linkages, and combinations thereof; and
b) from 20 to 80 weight % of a polyetherimide having a weight average molecular weight of 10,000 to 80,000 Daltons.

Embodiment 2

The sterilized article of Embodiment 1, wherein after exposure to 300 cycles of the hydrogen peroxide plasma sterilization using a mixture of hydrogen peroxide vapor and hydrogen peroxide plasma for 30 minutes at 20 to 55° C., the color of the polymer composition of the article exhibits a color shift of delta E of 10 units or less relative to the color of the polymer composition of the article before the first hydrogen peroxide plasma sterilization cycle, wherein delta E is measured in accordance with ASTM D2244-05.

Embodiment 3

The sterilized article of Embodiment 1 or 2, wherein after 300 cycles of the hydrogen peroxide plasma exposure the article has a weight loss of less than 5% of its initial weight before hydrogen peroxide plasma exposure.

Embodiment 4

The sterilized article of any of the preceding Embodiments, wherein after exposure to 150 cycles of the hydrogen peroxide plasma sterilization using a mixture of hydrogen peroxide vapor and hydrogen peroxide plasma for 30 minutes at 20 to 55° C., the color of the polymer composition exhibits a color shift of delta E of 10 units or less relative to the color of the polymer composition before the first hydrogen peroxide plasma sterilization cycle, wherein delta E is measured in accordance with ASTM D2244-05 and an article molded from the composition (i) initially also exhibits a multiaxial impact energy of greater than or equal to 45 ft-lbs (61 Joules) and (ii) after 150 cycles hydrogen peroxide plasma exposure has a multiaxial impact energy of greater than or equal to 20 ft-lbs (27 Joules) and multiaxial impact energy is determined according to ASTM D5628-10 at 23° C.

Embodiment 5

The sterilized article of Embodiment 1, wherein the delta E of the polymer composition after the exposure to 100 cycles of hydrogen peroxide plasma sterilization is less than 5 units.

Embodiment 6

The sterilized article of Embodiment 1, wherein the delta E of the polymer composition is 10 units or less after exposure of the article to 100 to 200 sterilization cycles, wherein each cycle is from 10 to 60 minutes at 20 to 55° C.

Embodiment 7

The sterilized article of Embodiment 6, wherein the delta E of the polymer composition after the exposure of the article to 100 to 200 sterilization cycles is less than 5 units.

Embodiment 8

The sterilized article of Embodiment 1, wherein the delta E of the polymer composition after the exposure to 100 cycles of hydrogen peroxide plasma sterilization is less than a delta E of a second article comprising the same polymer composition without the polyetherimide, wherein the delta E of the second article is measured after exposure to 100 cycles of hydrogen peroxide plasma sterilization under the same conditions, relative to the color of the second article measured before the first hydrogen peroxide plasma sterilization cycle.

Embodiment 9

The sterilized article of Embodiment 8, wherein the delta E of the polymer composition is less than the delta E of the second article, after each has been exposed to the same conditions, wherein the conditions include 100 to 200 sterilization cycles, wherein each cycle is from 10 to 60 minutes at 20 to 55° C.

Embodiment 10

The sterilized article of any of the preceding Embodiments, wherein at least a portion of the polymer composition has an etching, and wherein the etching is legible when observed from a distance of 0.3 meters without magnification after the exposure of the article to 100 cycles of hydrogen peroxide plasma sterilization.

Embodiment 11

The sterilized article of Embodiment 10, wherein the etching is legible when observed from a distance of 0.3 meters without magnification after exposure of the article to 100 to 200 sterilization cycles, wherein each cycle is from 10 to 60 minutes at 20 to 55° C.

Embodiment 12

The sterilized article of any of the preceding Embodiments, wherein the polymer composition comprises from 30 to 70 weight % of the polyphenylene ether sulfone; and from 70 to 30 weight % of the polyetherimide.

Embodiment 13

The sterilized article of Embodiment 12, wherein the polymer composition comprises from 40 to 60 weight % of the polyphenylene ether sulfone; and from 60 to 40 weight % of the polyetherimide.

Embodiment 14

The sterilized article of Embodiment 12, wherein the polymer composition comprises from 20 to 40 weight % of the polyphenylene ether sulfone; and from 80 to 60 weight % of the polyetherimide.

Embodiment 15

The sterilized article of any of the preceding Embodiments, wherein the polyetherimide comprises repeating units of the formula

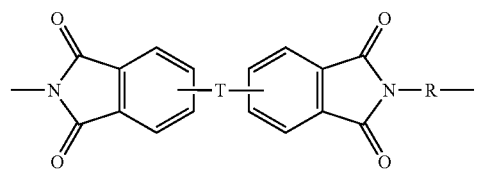

wherein R is a divalent radical of the formulae

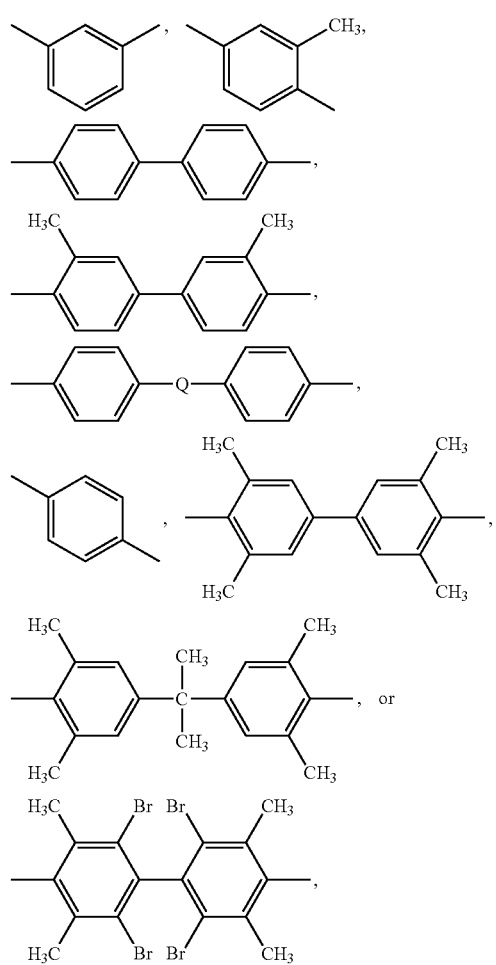

or combinations thereof wherein Q is selected from —O—, —S—, —C(O)—, —SO$_2$—, —SO—, and —C$_y$H$_{2y}$— wherein y is an integer from 1 to 5; and T is —O— or a group of the formula —O—Z—O— wherein the divalent bonds of the —O— or the —O—Z—O— group are in the 3,3', 3,4', 4,3', or the 4,4' positions and Z is R is a divalent group of the formula

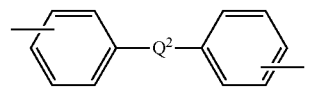

wherein $Q^2$ is selected from —O—, —S—, —C(O)—, —SO$_2$—, —SO—, and —C$_y$H$_{2y}$— wherein y is an integer from 1 to 5.

Embodiment 16

The sterilized article of any of the preceding Embodiments, wherein the polyetherimide has less than 5 ppm of free bisphenol A.

Embodiment 17

The sterilized article of any of the preceding Embodiments, wherein the polyphenylene ether sulfone is a copolymer of the following structure:

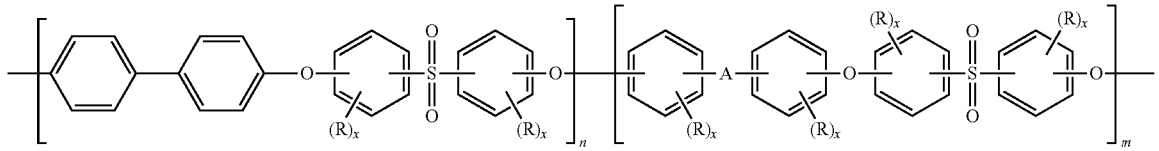

wherein n>m and n+m is 25 to 1000, R is selected from a C$_{1-8}$ alkyl, aryl, alkylaryl, alkoxy, halogen, and combinations thereof, x is 0 to 4, the aryl sulfone linkages are selected from 4,4' linkages, 3,3' linkages, 3,4' linkages, and combinations thereof, A is selected from —O—, —S—, —SO$_2$—, C$_{6-18}$ aryl, C$_{3-12}$ alkyl, and combinations thereof, and linkages of A to the aryl groups are selected from 4,4' linkages, 3,3' linkages, 3,4' linkages, and combinations thereof.

Embodiment 18

The sterilized article of Embodiment 17, wherein each x is 0.

Embodiment 19

The sterilized article of any of the preceding Embodiments, wherein the polyetherimide comprises less than 50 ppm amine end groups, the polyphenylene ether sulfone has less than 50 ppm hydroxyl groups, and the polyphenylene ether sulfone is methyl ether end-capped.

Embodiment 20

The sterilized article of any of the preceding Embodiments, wherein the polymer composition further comprises, based on the weight of the polymer composition, 0.1 to 20.0 weight % of a colorant selected from rutile titanium dioxide, anatase titanium dioxide, coated titanium dioxide, passivated titanium dioxide, and encapsulated titanium dioxide, wherein the titanium dioxide has a particle size of from 0.1 to 10 micrometers.

Embodiment 21

The sterilized article of any of the preceding Embodiments, wherein the polymer composition further comprises a colorant selected from carbon black, solvent red 52, solvent violet 36, solvent violet 13, pigment brown 24, pigment blue 29, pigment blue 15:4, or combinations thereof.

Embodiment 22

The sterilized article of any of the preceding Embodiments, wherein the polymer composition further comprises, based on the weight of the polymer composition, at least 0.01 weight % of a phosphorous containing stabilizer having a molecular weight of at least 300 Daltons.

Embodiment 23

The sterilized article of Embodiment 22, wherein the phosphorous stabilizer is selected from aryl phosphites and aryl phosphonates.

Embodiment 24

The sterilized article of any of the preceding Embodiments, wherein the polymer composition further comprises, based on the weight of the polymer composition, at least 0.05 weight % of a mold release agent selected from C6 to C36 alkyl carboxylic esters, C6 to C36 alkyl carboxylic acids, C6 to C36 alkyl carboxylic acid salts, C6 to C36 alkyl amides, and polyolefins.

Embodiment 25

The sterilized article of any of the preceding Embodiments, wherein the article is selected from a molded part, sheet, slab, profile, film, and fiber.

Embodiment 26

The sterilized article of any of the preceding Embodiments, wherein the article is selected from a medical device, dental device, surgical device, sterilization device, decontamination device, food handling device, food preparation device, beverage handling device, beverage preparation device, or a component thereof.

Embodiment 27

The sterilized article of any of the preceding Embodiments, wherein the article is selected from a container, a syringe body, a tray, an animal cage, an endoscope, a ureteroscope catheters, clamps, cables, telescopes, forceps, scissors, and a drill.

Embodiment 28

The sterilized article of any of the preceding Embodiments, wherein the article further comprises a biocidal additive component.

Embodiment 29

The sterilized article of Embodiment 28, wherein the biocidal additive component is selected from metals, inorganic compounds, and organic compounds.

Embodiment 30

The sterilized article of Embodiment 29, wherein the biocide is selected from germicides, antibiotics, antibacterials, antivirals, antifungals, antiprotozoals, antiyeasts, antialgals, antiparasites, and combinations thereof.

Embodiment 31

The sterilized article of any of the preceding Embodiments, wherein the tensile strength at yield of the article after 150 hydrogen peroxide plasma sterilization cycles is at least 12,000 psi (82.8 MPa).

Embodiment 32

A sterilized article comprising a sterilized polymer composition, treated with a member selected from hydrogen peroxide plasma, hydrogen peroxide vapor, and combinations thereof, the polymer composition comprising a) from 80 to 20 weight % of a polyphenylene ether sulfone having a weight average molecular weight of 10,000 to 80,000 Daltons; the polyphenylene ether sulfone having the formula

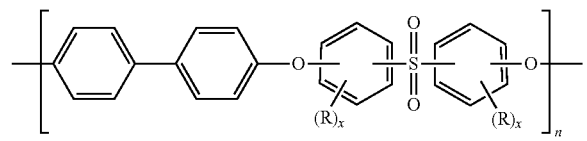

wherein n is 25 to 1000, R is selected from $C_{1-8}$ alkyl, aryl, alkyl aryl, alkoxy, halogen, and combinations thereof, x is 0 to 4, and the aryl sulfone linkages are selected from 4,4' linkages, 3,3' linkages, 3,4' linkages, and combinations thereof; and b) from 20 to 80 weight % of a polyetherimide having a weight average molecular weight of 10,000 to 80,000 Daltons; wherein after exposure to 150 cycles of the hydrogen peroxide plasma sterilization using a mixture of hydrogen peroxide vapor and hydrogen peroxide plasma for 30 minutes at 20 to 55° C., the color of the polymer composition exhibits a color shift of delta E of 10 units or less relative to the color of the polymer composition color before the first hydrogen peroxide plasma sterilization cycle; wherein delta E is measured in accordance with ASTM D2244-05 and an article molded from the composition (i) initially also exhibits a multiaxial impact energy of greater than or equal to 45 ft-lbs (61 Joules) and (ii) after 150 cycles hydrogen peroxide plasma exposure has a multiaxial impact energy of greater than or equal to 20 ft-lbs (27 Joules) and multiaxial impact energy is determined according to ASTM D5628-10 at 23° C.; wherein at least a portion of the polymer composition has an etching, and wherein the etching is legible when observed from a distance of 0.3 meters without magnification after the exposure of the article to 100 cycles of hydrogen peroxide plasma sterilization.

The invention is further illustrated by the following non-limiting examples.

EXAMPLES

Materials

The materials employed to prepare samples for use in the Examples and Comparative Examples are identified in Table 1.

TABLE 1

| Material | Description | Source |
|---|---|---|
| PEI* | ULTEM 1000 Polyetherimide (Mw = 55,000 (GPC, PS standards), refractive index = 1.6586 (measured at 633 nanometers and 23° C.), Tg = 221° C.) PEI less than 20 ppm amine end groups | SABIC Innovative Plastics |
| PPSU | RADEL R5100 Polyphenylene Ether Sulfone (Mw = 49,600 (GPC, PS standards), refractive index = 1.6673 (measured at 633 nanometers at 23° C.), Tg = 224° C.) less than 20 ppm phenolic OH end groups | Solvay Co. |
| Solvent Red 52 | 3-Methyl-6-(p-toluidino)-3H-dibenz[f,ij]isoquinoline-2,7-dione | Lanxess |
| Solvent Violet 36 | 1,8-bis-(p-toluidino)-9,10-anthraquinone | Lanxess |
| Solvent Violet 13 | 1-hydroxy-4-(p-toluidino)-9,10-anthraquinone | Lanxess |
| Titanium Dioxide | Pigment White 6, a rutile silica-alumina encapsulated $TiO_2$ (0.24 micron diameters) | DuPont |
| Pigment Brown 24 | Chrome Antimony Titanium Brown | BASF |
| Pigment Blue 29 | Ultramarine Blue | Lanxess |
| Pigment Black 7 | Carbon Black | Cabot |
| Pigment Blue 15:4 | Copper Phthalocyanine Blue | Sun Chemical |

*contains 0.1 weight percent tris (di-2,4-tert butyl phenyl) phosphite (IRGAPHOS 168)

Techniques and Procedures

Compositions were prepared by extruding combinations of the polyphenylene ether sulfones and polyetherimides in a 2.5 inch (63.5 mm) single-screw vacuum vented extruder. Compositions are listed in weight percent based on the total weight of the composition except where noted otherwise. The extruder was set at about 325 to 360° C. The compositions were run at about 180 rotations per minute (rpm) under vacuum using a mild mixing screw; vacuum was approximately 20 inches (508 mm) of mercury (Hg). In some instances the blend was melt filtered using a 40 micrometers filter. The extrudate was cooled, pelletized, and dried at 135° C. Test samples were injection molded at a set temperature of 350 to 375° C. and mold temperature of 150° C., a screw speed of approximately 60 rpm, with 50 psi (0.345 MPa) back pressure using a 30 seconds cycle time.

Gel permeation chromatography (GPC) was done as per ASTM D5296-05, polystyrene standards were used for calibration. Tensile strength was measured on injection molded bars as per ASTM D638-03 at 0.2 inches (12.7 mm)/minute crosshead speed. Tensile strength is reported at yield (Y), percent elongation (% E) is reported at break. Weight loss was measured by comparing the weight of bars before and after 150 and 300 hydrogen peroxide plasma sterilization cycles using an analytical balance accurate to at least 0.01 grams.

The reported value is an average of at least 4 samples. Percent transmission (% T) was measured on 3.2 mm thick injection molded parts as per ASTM D1003-7 using a D65 illuminant with a 10 degree observer angle. Multiaxial impact (MAI) was run on 3.2×102 mm injection molded discs as per ASTM 56280-10 the total energy is reported as Joules (J) and foot-pounds (ft-lbs). Glass transition temperature (Tg) was measured by DSC on the second scan using a heating rate of 20° C./min.

Color Chip Sterilization Testing—Test chips were loaded and cycled in a STERRAD® NX or 100NX hydrogen peroxide sterilization chamber (manufactured by Advanced Sterilization Products, Division of Ethicon Inc.) to evaluate the materials ability to retain its color and properties. The materials were run for the indicated number of sterilization cycles and then removed for evaluation. Each cycle time consisted of 2 stages for a total time of 30 minutes at a temperature from 20 to 55° C. with at least 4 minutes exposure to a hydrogen peroxide derived gas plasma per stage. Each stage of a cycle involved a 0.5 min. injection, 7.0 minute transfer, 0.5 min diffusion and a 4.0 minute plasma exposure. A spectrophotometer was used at a 10 degree observation angle under illumination at a 65 degree angle to measure color indices (L*, a*, b*) of each color chip, at three reported points in time: as molded; 100 cycles; and 150 cycles. The changes in value of (L*, a*, b*) over the reported number of cycles are determined (dL, da, db) and then summed $((dL^2+da^2+db^2)^{1/2}$ delta E) to produce the value reported under delta E. Color was measured using a COLOREYE 7000A instrument from GretagMacbeth as per ASTM D2244-05. In addition, a BYK Gardner micro Tri-gloss meter was used to evaluate surface gloss at 60 and 85 degrees as per ASTM method D 523-08 and reported in gloss units. Color coordinates, transmittance, & haze were determined using a MacBeth CE7000 spectrophotometer. This instrument uses a Xenon flash light source. Wavelength monitoring and detection range is from 360 nm to 760 nm. CIELab color coordinates for opaque and translucent samples are calculated assuming illuminate D65 and 10 degree observer. Transmittance is the Y color coordinate in the 1931 tristimulus scale with illuminate C & 2 degree observer. Haze is the % scattered light/total transmission. This is determined in a two step measurement sequence using a white standard and a light trap. Transmittance and haze measurements apply to clear and translucent samples only.

The hydrogen peroxide vapor exposure was done using an AMSCO V-PRO low temperature sterilization system by STERIS Co. The sterilization cycle comprises a conditioning phase where a vacuum pulse is used to remove air and moisture from the chamber followed by a sterilization phase where a hydrogen peroxide vapor is drawn and held in the chamber in a series of vacuum pulses and is in contact with the article (at least a portion of which comprises a PPSU-PEI blend). The temperature varied from 20 to 50° C. After a programmed time the vapor is removed and the chamber aerated and brought to atmospheric pressure.

The STERRAD NX, 100NX and STERIS AMSCO V-PRO sterilization systems both employ hydrogen peroxide as the sterilant. The STERRAD NX concentrates liquid hydrogen peroxide to form a hydrogen peroxide vapor that is at least partially in a plasma form. The STERIS V-PRO Sterilizer forms a hydrogen peroxide vapor with little or no plasma.

Examples 1-3 and Comparative Examples A-C

These materials were combined in the proportions specified in Table 2 to produce the six classes of experimental samples. The PPSU and PEI/PPSU blends were formulated (color matched) so that the resultant articles had the same white, gray or blue colors as molded. PPSU is end capped with methyl ether end groups and has phenolic OH end group content below 20 ppm.

TABLE 2

| Color Formulations | 4/30 g/lb of polymer (g/0.454 kg) | |
|---|---|---|
| White | Ex. 1 | Comp. Ex. A |
| Polymer | 60 PEI:40 PPSU | PPSU |
| Solvent Red 52 | 0.009 | 0.0045 |
| Titanium Dioxide | 41.0 | 33.0 |
| Pigment Brown 24 | 0.04 | 0.155 |
| Pigment Blue 29 | 0.42 | 0.35 |
| Gray | Ex. 2 | Comp. Ex. B |
| Polymer | 60 PEI:40 PPSU | PPSU |
| Solvent Violet 36 | 0.044 | 0.027 |
| Titanium Dioxide | 19.0 | 18.0 |
| Pigment Black 7 | 0.09 | 0.09 |
| Pigment Blue 29 | 0.42 | 0.50 |
| Pigment Brown 24 | 0.37 | 0.5 |
| Blue | Ex. 3 | Comp. Ex. C |
| Polymer | 60 PEI:40 PPSU | PPSU |
| Solvent Violet 13 | 0.18 | 0.16 |
| Titanium Dioxide | 5.8 | 5.15 |
| Pigment Blue 15:4 | 0.38 | 0.33 |
| Pigment Brown 24 | none | 0.20 |

Examples 1, 2, and 3 are compositions according to the present invention that contain 60 parts polyetherimide and 40 parts polyphenylene ether sulfone per 100 parts polymer, along with the other listed ingredients in the indicated amounts measured in grams per pound of polymer. Comparative Examples A, B, and C contain 100 parts polyphenylene ether sulfone per 100 parts polymer, along with the other listed ingredients in the indicated amounts measured in grams per pound of polymer. Together these samples present comparisons of a pigmented polyetherimide/polyphenylene ether sulfone blend according to the invention against a similarly pigmented polyphenylene ether sulfone composition: Example 1 and Comparative Example A are white; Example 2 and Comparative Example B are gray; and Example 3 and Comparative Example C are blue.

These samples were evaluated according to the stated procedures and results are reported in Table 3.

TABLE 3

| | | Color & Gloss vs. Peroxide Plasma Exposure | | | | | |
|---|---|---|---|---|---|---|---|
| Example | Description | Delta E | L* | a* | b* | 60 Degree Gloss | 85 Degree Gloss |
| A | PPSU - white as molded | 0.0 | 86.8 | −2.0 | −1.4 | 106.7 | 97.7 |
| | PPSU - white 100 cycles | 25.8 | 82.4 | 0.5 | 23.9 | 4.3 | 59.9 |
| | PPSU - white 150 cycles | 37.3 | 78.3 | 5.9 | 34.1 | 4.0 | 46.4 |

TABLE 3-continued

Color & Gloss vs. Peroxide Plasma Exposure

| Example | Description | Delta E | L* | a* | b* | 60 Degree Gloss | 85 Degree Gloss |
|---|---|---|---|---|---|---|---|
| | PPSU - white 200 cycles | 36.3 | 77.6 | 6.5 | 32.7 | 1.5 | 2.6 |
| | PPSU - white 300 cycles | 36.4 | 78.5 | 5.8 | 33.2 | 1.4 | 1.1 |
| B | PPSU - gray as molded | 0.0 | 66.6 | −1.0 | −2.0 | 106.7 | 97.8 |
| | PPSU - gray 100 cycles | 13.9 | 66.4 | −1.2 | 11.9 | 24.8 | 76.1 |
| | PPSU - gray 150 cycles | 25.6 | 64.6 | 1.4 | 23.4 | 3.5 | 46.2 |
| | PPSU - gray 200 cycles | 27.2 | 63.9 | 2.6 | 24.9 | 1.5 | 15.5 |
| | PPSU - gray 300 cycles | 33.6 | 61.7 | 4.5 | 30.8 | 1.1 | 1.6 |
| C | PPSU - blue as molded | 0.0 | 52.7 | −12.1 | −24.5 | 107.1 | 96.4 |
| | PPSU - blue 100 cycles | 24.7 | 53.5 | −14.1 | 0.1 | 33.9 | 85.1 |
| | PPSU - blue 150 cycles | 40.6 | 54.5 | −9.9 | 16.0 | 19.1 | 69.6 |
| | PPSU - blue 200 cycles | 37.3 | 51.6 | −12.8 | 12.8 | 0.9 | 2.8 |
| | PPSU - blue 300 cycles | 50.6 | 52.7 | −12.1 | −24.5 | 0.8 | 1.5 |
| 1 | 60:40 PEI:PPSU - white as molded | 0.0 | 87.1 | −2.6 | −1.2 | 103.8 | 97.5 |
| | 60:40 PEI:PPSU - white 100 cycles | 1.2 | 87.6 | −2.7 | −0.2 | 13.3 | 67.6 |
| | 60:40 PEI:PPSU - white 150 cycles | 3.9 | 87.0 | −3.0 | 2.6 | 37.4 | 86.6 |
| | 60:40 PEI:PPSU - white 200 cycles | 4.9 | 86.9 | −3.1 | 3.6 | 56.4 | 92.5 |
| | 60:40 PEI:PPSU - white 300 cycles | 5.9 | 87.0 | −3.3 | 4.6 | 17.6 | 81.5 |
| 2 | 60:40 PEI:PPSU - gray as molded | 0.0 | 66.5 | −1.0 | −2.2 | 105.9 | 99.0 |
| | 60:40 PEI:PPSU - gray 100 cycles | 0.7 | 67.8 | −1.2 | −1.7 | 24.0 | 69.8 |
| | 60:40 PEI:PPSU - gray 150 cycles | 2.2 | 68.0 | −1.4 | −0.7 | 8.8 | 60.1 |
| | 60:40 PEI:PPSU - gray 200 cycles | 3.2 | 67.7 | −1.6 | 0.7 | 44.4 | 90.2 |
| | 60:40 PEI:PPSU - gray 300 cycles | 4.4 | 68.4 | −1.8 | 1.7 | 9.4 | 71.0 |
| 3 | 60:40 PEI:PPSU - blue as molded | 0.0 | 52.9 | −12.5 | −25.5 | 110.5 | 99.2 |
| | 60:40 PEI:PPSU - blue 100 cycles | 1.4 | 53.0 | −13.1 | −24.2 | 60.2 | 90.9 |
| | 60:40 PEI:PPSU - blue 150 cycles | 4.0 | 52.5 | −13.5 | −21.7 | 68.0 | 95.8 |
| | 60:40 PEI:PPSU - blue 200 cycles | 5.1 | 52.7 | −14.0 | −20.6 | 73.1 | 95.7 |
| | 60:40 PEI:PPSU - blue 300 cycles | 5.7 | 52.7 | −13.7 | −20.0 | 54.0 | 90.9 |

The PEI/PPSU compositions according to the invention demonstrate strong performance in retaining color after repeated sterilization in peroxide plasma and showed a significant improvement in color stability compared to PPSU after 100, 150, 200, and 300 hydrogen peroxide plasma sterilization cycles. Large delta E shifts were observed after 100 cycles for PPSU samples of Comparative Examples A (25.8), B (13.9), and C (24.7), as compared to the surprisingly much lower delta E shifts observed in the PEI/PPSU blend according to the present invention: Example 1 (1.2), Example 2 (0.7), and Example 3 (1.4), respectively. A large increase in delta E is a numerical representation of extent of color change, with 0 being a "no-change" condition. Higher numbers of sterilization cycles give even greater differences in color shift between the PPSU Comparative Examples and the PEI-PPSU blends.

Example 4 and Comparative Example D

Test chips were prepared from unpigmented, natural color polymer according to the invention, 60 parts polyimide and 40 parts polyphenylene ether sulfone per 100 parts polymer, referred to as Example 4; and 100 parts polyphenylene ether sulfone per 100 parts polymer, referred to as Comparative Example D. These samples were evaluated as molded and after 150 hydrogen peroxide plasma sterilization cycles, the results are reported in Table 4.

TABLE 4

Appearance and Properties vs. Peroxide Plasma Exposure

| Ex. | Description | Delta E | L* | a* | b* | Tensile Strength Kpsi | % Elong at Break | MAI Total Energy J | Tg (° C.) (DSC) | % Wt. Loss | Mw |
|---|---|---|---|---|---|---|---|---|---|---|---|
| D | PPSU clear (as molded) | 0.0 | 83.0 | 0.9 | 25.9 | 9.4 (64.8 MPa) | 93 | 84.0 | 222.1 | 0 | 50,140 |
| | PPSU clear (150 Cycles) | 47.7 | 60.5 | 12.7 | 66.3 | 7.5 (51.7 MPa) | 11 | 20.4 | 222.2 | 2.25% | 48,000 |
| 4 | 60:40 PEI:PPSU clear (as molded) | 0.0 | 81.6 | −2.3 | 43.6 | 13.0 | 98 | 92.6 | 218.2 | 0 | 51,200 |
| | 60:40 PEI:PPSU clear (150 cycles) | 0.8 | 82.1 | −2.3 | 44.3 | 12.7 | 92 | 91.5 | 218.3 | 0.01% | 50,690 |

The unpigmented, natural color sample, Example 4, demonstrated strong color retention after 150 cycles of peroxide plasma treatment as indicated by a delta E of only 0.8. In marked contrast, the unpigmented natural color PPSU sample, Comparative Example D, exhibited a much higher delta E of 47.7. The PEI/PPSU blend according to the invention, Example 4, also showed superior retention of tensile strength and % elongation at break after 150 cycles of peroxide plasma treatment when compared to the PPSU sample, Comparative Example D.

The GPC analyses of Example 4 show that the PEI/PPSU blend according to the invention retained a higher % of Mw, than the PPSU control, Comparative Example D. The multi-axial impact (MAI) of Example 4 is still above 60 Joules (J) after 150 cycles showing ductile failure while the PPSU Comparative Example shows brittle failure with a low MAI. The glass transition temperature (Tg) is above 200° C.

Testing bars were molded from the blend of 60 parts polyetherimide (PEI) and 40 parts polyphenylene ether sulfone per 100 parts polymer according to the invention, referred to as Example 4; and 100 parts polyphenylene ether sulfone per 100 parts polymer, referred to as Comparative Example D. The samples were given identifying markings etched into the surface with a metal stylus. They were subjected to 150 cycles of peroxide plasma sterilization, and then weighed and visually inspected.

The PEI/PPSU samples of Example 4 retained 99.99% of their weight compared to control samples, while the PPSU samples of Comparative Example D retained only 97.75% of their weight compared to control samples.

Markings were etched into the surface of all samples. However, after 150 cycles, the etched markings were gone from the surface of the PPSU samples of Comparative Example D, while the PEI/PPSU samples, Example 4 according to the invention, retained their etched identifying markings.

The samples of Example 4 thus exhibited surprisingly better overall condition after 150 cycles of peroxide plasma sterilization than the PPSU samples. In addition, the PPSU samples had discolored toward red/orange while the samples of Example 4 retained their appearance.

Examples 5 to 9 and Comparative Examples E, F and G

In Examples F, G, and 5 to 9 the ratio of PPSU to PEI was varied from 95:5 wt. % to 40:60 wt. %. These clear blends were compared to the 100% PPSU (Comparative Example E) after exposure to a hydrogen peroxide plasma in a STERRAD 100NX sterilization device for, 100, 150, 200, and 300 cycles.

The delta E color formation after 100 cycles is sharply reduced showing less change in color vs. the PPSU control example E. With 20 wt. % or more of PEI (Examples 5 to 9) the delta E after only 100 cycles drops from 10.0 for PPSU to 2.1 or less for the PEI-PPSU blends showing almost no perceptible color change to the human eye. After 300 cycles the difference in color (delta E) with 30 wt. % or more PEI (examples 6 to 9) is reduced by more than 10 times compared to blends with less PEI (Comparative Examples F and G). With 30 wt. % PEI or more (Examples 6 to 9) there is no loss of the as molded % transmission on peroxide plasma exposure. Low levels (5 and 10 wt. %) of PEI, as in Comparative Examples F and G, are not very effective in reducing color formation.

In Table 6 the same compositions as Table 5 were evaluated for their retention of tensile properties after 150 cycles of peroxide plasma sterilization. The tensile strength at yield (Y) and break (B) as well as the percent elongation at break show much higher retention of the as molded values with added PEI, this is especially noticeable with 20 wt. % or more PEI (Examples 5 to 9). Also note that blends with 20% or more PEI have higher tensile strength and modulus than PPSU (Comparative Example E), with 40 wt. % or more PEI tensile strength at yield is above 12,000 psi (82.7 MPa) before and after 150 sterilization cycles.

Under hydrogen peroxide plasma sterilization the PPSU molded articles show weight loss as well as loss of optical properties, tensile strength, and elongation. With 20 wt. % or more PEI (Examples 5 to 9) the weight loss after 150 and 300 cycle is reduced. At 30 wt. % or more PEI (Examples 6 to 9) weight loss after 300 sterilization cycles is less than 1% of the initial part weight.

TABLE 5

Color, Haze & Transmission vs. Peroxide Plasma Exposure

| | Example | | | | | | | |
|---|---|---|---|---|---|---|---|---|
| | E | F | G | 5 | 6 | 7 | 8 | 9 |
| PPSU natural | 100 | 95 | 90 | 80 | 70 | 60 | 50 | 40 |
| PEI natural | | 5 | 10 | 20 | 30 | 40 | 50 | 60 |
| Delta E as molded | 0.0 | 0.0 | 0.0 | 0.0 | 0.0 | 0.0 | 0.0 | 0.0 |
| Delta E 100 cycles | 10.0 | 13.1 | 9.7 | 2.1 | 1.9 | 1.8 | 1.6 | 2.3 |
| Delta E 150 cycles | 16.6 | 25.8 | 21.0 | 9.6 | 2.5 | 2.6 | 1.7 | 2.5 |
| Delta E 200 cycles | 24.1 | 34.4 | 32.8 | 16.0 | 2.3 | 2.4 | 2.1 | 2.9 |
| Delta E 300 cycles | 34.4 | 49.4 | 44.6 | 28.0 | 2.6 | 2.6 | 2.2 | 3.2 |
| CE % Haze as molded | 5.1 | 3.6 | 3.4 | 2.9 | 2.8 | 5.5 | 6.2 | 6.8 |
| CE % Haze 100 cycles | 83.7 | 51.9 | 45.8 | 23.6 | 17.0 | 17.4 | 13.7 | 9.5 |
| CE % Haze 150 cycles | 91.7 | 64.8 | 84.2 | 43.5 | 16.6 | 20.9 | 24.0 | 17.2 |
| CE % Haze 200 cycles | 98.5 | 101.8 | 101.7 | 79.8 | 23.5 | 42.4 | 56.6 | 46.2 |
| CE % Haze 300 cycles | 99.6 | 102.2 | 102.2 | 98.9 | 42.9 | 50.8 | 55.4 | 58.1 |
| % T as molded (3.2 mm) | 68.7 | 61.1 | 58.6 | 56.4 | 50.1 | 52.3 | 52.4 | 49.7 |
| % Retention % T 100 cycles | 83.6 | 77.7 | 79.5 | 96.8 | 100.0 | 100.0 | 100.0 | 100.0 |
| % Retention % T 150 cycles | 76.9 | 51.5 | 60.8 | 81.6 | 100.0 | 100.0 | 100.0 | 100.0 |
| % Retention % T 200 cycles | 78.9 | 43.0 | 60.8 | 64.4 | 100.0 | 100.0 | 100.0 | 100.0 |
| % Retention % T 300 cycles | 64.6 | 31.2 | 33.1 | 47.0 | 100.0 | 100.0 | 100.0 | 100.0 |

TABLE 6

Tensile Properties and Weight Loss vs. Peroxide Plasma Exposure

| | Example | | | | | | | |
|---|---|---|---|---|---|---|---|---|
| | E | F | G | 5 | 6 | 7 | 8 | 9 |
| PPSU natural | 100 | 95 | 90 | 80 | 70 | 60 | 50 | 40 |
| PEI natural | | 5 | 10 | 20 | 30 | 40 | 50 | 60 |
| T. Mod as molded psi | 318000 | 313000 | 315000 | 332000 | 359000 | 375000 | 395000 | 401000 |
| (MPa) | (219.3) | (215.8) | (217.2) | (228.9) | (247.5) | (258.6) | (272.3) | (276.5) |
| T. Str (Y) as molded psi | 11000 | 10270 | 10890 | 10980 | 11470 | 12270 | 12870 | 13200 |
| | (75.8) | (70.8) | (75.1) | (75.7) | (79.1) | (84.6) | (88.7) | (91.0) |
| T. Str (B) as molded psi | 10300 | 9860 | 10080 | 10850 | 10270 | 11320 | 12400 | 12570 |
| | (71.0) | (68.0) | (69.5) | (74.8) | (70.8) | (78.0) | (85.5) | (86.7) |
| Elong. (B) as molded % | 92 | 91 | 89 | 93 | 68 | 73 | 88 | 84 |
| T. Str (Y) 150 cycles psi | 10480 | 10030 | 10240 | 10860 | 11460 | 12140 | 12830 | 13380 |
| | (72.3) | (69.2) | (70.6) | (74.9) | (79.0) | (83.7) | (88.5) | (92.3) |
| T. Str (B) 150 cycles psi | 8380 | 7760 | 7980 | 8620 | 10540 | 10560 | 10040 | 12600 |
| | (57.8) | (53.5) | (55.0) | (59.4) | (72.7) | (72.8) | (69.2) | (86.9) |
| Elong. (B) 150 cycles % | 12 | 14 | 18 | 32 | 74 | 67 | 30 | 86 |
| % wt loss 150 cycles | 2.09 | 1.52 | 1.47 | 0.42 | 0.05 | 0.21 | 0.09 | 0.25 |
| % wt loss 300 cycles | 8.25 | 7.52 | 5.42 | 2.14 | 0.71 | 0.89 | 0.41 | 0.60 |

T. Mod. = tensile modulus;
T. Str.—tensile strength

Examples 10 to 12 and Comparative Examples H, I, J and K

In further examples the PPSU-PEI blends were exposed to sterilization in a hydrogen peroxide vapor in a STERIS AMSCO V-PRO low temperature (20 to 50° C.) sterilization system using a 55 minute cycle (the "Lumen Cycle" using 59% hydrogen peroxide). The STERRAD NX, 100NX, and STERIS AMSCO V-PRO sterilization systems both employ hydrogen peroxide as the sterilant. The STERRAD NX concentrates liquid hydrogen peroxide to form a hydrogen peroxide vapor that is at least partially in a plasma form. The STERIS V-PRO Sterilizer forms a hydrogen peroxide vapor with little or no plasma. The hydrogen peroxide vapor is less aggressive than the plasma but still caused damage to PPSU.

Table 7 shows the color change of the white, gray, and blue formulations of Table 2 after 300 cycles of hydrogen peroxide vapor exposure. The PPSU Comparative Examples H, I, and J show a large color shift, with a delta E greater than 10, surprisingly the 60:40 PEI:PPSU blends (Examples 10 to 12) show a delta E of less than 2.

TABLE 7

Color vs. Peroxide Vapor Exposure

| Example | Description | Delta E | L* | a* | b* |
|---|---|---|---|---|---|
| H | PPSU - white as molded | 0.0 | 87.1 | -2.5 | -0.7 |
| | PPSU - white 200 cycles | 4.5 | 87.2 | -3.2 | 3.8 |
| | PPSU - white 300 cycles | 29.3 | 81.1 | 3.9 | 27.2 |
| I | PPSU - gray as molded | 0.0 | 66.7 | -1.0 | -2.0 |
| | PPSU - gray 200 cycles | 1.5 | 67.3 | -1.3 | -0.6 |
| | PPSU - gray 300 cycles | 10.2 | 67.2 | -1.3 | 8.2 |
| J | PPSU - blue as molded | 0.0 | 52.2 | -11.0 | -25.9 |
| | PPSU - blue 200 cycles | 20.2 | 53.7 | -16.1 | -6.4 |
| | PPSU - blue 300 cycles | 46.4 | 57.4 | -2.4 | 19.4 |
| 10 | 60:40 PEI:PPSU - white as molded | 0.0 | 87.2 | -2.6 | -0.9 |
| | 60:40 PEI:PPSU - white 200 cycles | 0.7 | 87.8 | -2.7 | -1.3 |
| | 60:40 PEI:PPSU - white 300 cycles | 0.8 | 87.9 | -2.8 | -0.9 |
| 11 | 60:40 PEI:PPSU - gray as molded | 0.0 | 66.4 | -1.1 | -2.1 |
| | 60:40 PEI:PPSU - gray 200 cycles | 0.8 | 67.1 | -1.2 | -1.9 |

TABLE 7-continued

Color vs. Peroxide Vapor Exposure

| Example | Description | Delta E | L* | a* | b* |
|---|---|---|---|---|---|
| | 60:40 PEI:PPSU - gray 300 cycles | 1.0 | 67.3 | -1.2 | -1.8 |
| 12 | 60:40 PEI:PPSU - blue as molded | 0.0 | 52.2 | -12.7 | -24.5 |
| | 60:40 PEI:PPSU - blue 200 cycles | 0.5 | 52.3 | -13.1 | -24.3 |
| | 60:40 PEI:PPSU - blue 300 cycles | 1.3 | 51.3 | -13.6 | -24.3 |

Transparent blends were also exposed to 300 cycles of hydrogen peroxide vapor sterilization. Table 8 shows the clear, uncolored PPSU control (Comparative Example K) undergoing a large change in color (delta E=38.3) as well as increasing in haze (6.6 to 22.5%) with a loss of transmission (67.6 to 53.1%). Surprisingly, under the same 300 cycles of sterilization, the clear 60:40 PEI:PPSU blend (Example 13) had a very small color change (delta E=1.5) and had almost no change in haze (8.0 to 9.9) and an increase in % T to 66.4%.

TABLE 8

Clear Resin Appearance vs. Peroxide Vapor Exposure

| Example | Description | Delta E | L* | a* | b* | CE % haze | % T |
|---|---|---|---|---|---|---|---|
| K | PPSU - clear as molded | 0.0 | 85.2 | 0.2 | 23.8 | 6.6 | 67.6 |
| | PPSU - clear 150 cycles | 1.8 | 86.8 | -0.4 | 24.1 | 7.2 | 71.0 |
| | PPSU - clear 300 cycles | 38.3 | 76.5 | 5.9 | 60.7 | 22.5 | 53.1 |
| 13 | 60:40 PEI:PPSU clear as molded | 0.0 | 82.9 | -2.5 | 44.7 | 8.0 | 63.8 |
| | 60:40 PEI:PPSU clear 150 cycles | 1.1 | 83.9 | -2.9 | 44.6 | 8.9 | 65.8 |
| | 60:40 PEI:PPSU clear 300 cycles | 1.5 | 84.3 | -3.1 | 44.9 | 9.9 | 66.4 |

Table 9 shows retention of multiaxial impact (MAI) strength, tensile strength at yield and % elongation at break for PPSU (Comparative Example L) and a 60:40 PEI-PPSU (Example 14) blend after 150 and 300 cycles hydrogen peroxide vapor exposure. After 300 cycles the PPSU sample (Comparative Example L) has only 13% elongation and has a brittle MAI failure with a total impact energy of only 12.8 ft-lbs (17.4 J). The PPSU-PEI blend (Example 14) after 300 sterilization cycles has elongation of 77% with a ductile MAI failure and a total impact energy of 64.0 ft-lbs (86.8 J).

TABLE 9

Mechanical Properties vs. Peroxide Vapor Exposure

| Ex. | Description | MAI Total Energy Ft-lbs | MAI Total Energy J | MAI Failure type | Tensile Str. (Y) psi (MPa) | % Elong @ Break |
|-----|-------------|-------------------------|---------------------|------------------|----------------------------|------------------|
| L | PPSU clear as molded | 57.0 | 77.3 | Ductile | 11990 (82.7) | 105 |
| | PPSU clear 150 cycles | 63.8 | 86.5 | Ductile | 10430 (71.9) | 100 |
| | PPSU clear 300 cycles | 12.8 | 17.4 | Brittle | 10020 (69.1) | 13 |
| 14 | 60:40 PEI:PPSU clear as molded | 68.3 | 92.6 | Ductile | 13200 (91.0) | 92 |
| | 60:40 PEI:PPSU clear 150 cycles | 71.3 | 96.6 | Ductile | 13210 (91.1) | 90 |
| | 60:40 PEI:PPSU clear 150 cycles | 64.0 | 86.8 | Ductile | 13120 (90.5) | 77 |

While the invention has been described with reference to several embodiments, it will be understood by those skilled in the art that various changes can be made and equivalents can be substituted for elements thereof without departing from the scope of the invention. In addition, many modifications can be made to adapt a particular situation or material to the teachings of the invention without departing from essential scope thereof. Therefore, it is intended that the invention not be limited to the particular embodiments disclosed as the best mode contemplated for carrying out this invention, but that the invention will include all embodiments falling within the scope of the appended claims.

What is claimed is:

1. A sterilized article comprising a sterilized polymer composition having an as molded color, treated with a member selected from hydrogen peroxide plasma, hydrogen peroxide vapor, and combinations thereof, the polymer composition comprising
   a) from 80 to 20 weight % of a polyphenylene ether sulfone; the polyphenylene ether sulfone having the formula

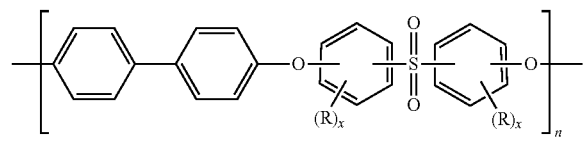

wherein
   n is 25 to 100
   R is selected from $C_{1-8}$ alkyl, aryl, alkyl aryl, alkoxy, halogen, and combinations thereof,
   x is 0 to 4 and
   the aryl sulfone linkages are selected from 4,4' linkages, 3,3' linkages, 3,4' linkages, and combinations thereof; and
   b) from 20 to 80 weight % of a polyetherimide, wherein after exposure to 300 cycles of the hydrogen peroxide plasma sterilization using a mixture of hydrogen peroxide vapor and hydrogen peroxide plasma for 30 minutes at 20 to 55° C., the color of the polymer composition of the article exhibits a color shift of delta E of 10 units or less relative to the as molded color of the polymer composition before the first hydrogen peroxide plasma sterilization cycle, wherein delta E is measured in accordance with ASTM D2244-05.

2. The sterilized article of claim 1, wherein after 300 cycles of the hydrogen peroxide plasma exposure the article has a weight loss of less than 5% of its initial weight before hydrogen peroxide plasma exposure.

3. The sterilized article of claim 1, wherein after exposure to 150 cycles of the hydrogen peroxide plasma sterilization using a mixture of hydrogen peroxide vapor and hydrogen peroxide plasma for 30 minutes at 20 to 55° C., the color of the polymer composition exhibits a color shift of delta E of 10 units or less relative to the color of the polymer composition before the first hydrogen peroxide plasma sterilization cycle, wherein delta E is measured in accordance with ASTM D2244-05 and an article molded from the composition (i) initially also exhibits a multiaxial impact energy of greater than or equal to 45 ft-lbs (61 Joules) and (ii) after 150 cycles hydrogen peroxide plasma exposure has a multiaxial impact energy of greater than or equal to 20 ft-lbs (27 Joules) and multiaxial impact energy is determined according to ASTM D5628-10 at 23° C.

4. The sterilized article of claim 1, wherein the delta E of the polymer composition after the exposure to 100 cycles of hydrogen peroxide plasma sterilization is less than 5 units.

5. The sterilized article of claim 1, wherein the delta E of the polymer composition is 10 units or less after exposure of the article to 100 to 200 sterilization cycles, wherein each cycle is from 10 to 60 minutes at 20 to 55° C.

6. The sterilized article of claim 5, wherein the delta E of the polymer composition after the exposure of the article to 100 to 200 sterilization cycles is less than 5 units.

7. The sterilized article of claim 1, wherein the delta E of the polymer composition after the exposure to 100 cycles of hydrogen peroxide plasma sterilization is less than a delta E of a second article comprising the same polymer composition without the polyetherimide, wherein the delta E of the second article is measured after exposure to 100 cycles of hydrogen peroxide plasma sterilization under the same conditions, relative to the color of the second article measured before the first hydrogen peroxide plasma sterilization cycle.

8. The sterilized article of claim 7, wherein the delta E of the polymer composition is less than the delta of the second article, after each has been exposed to the same conditions, wherein the conditions include 100 to 200 sterilization cycles, wherein each cycle is from 10 to 60 minutes at 20 to 55° C.

9. The sterilized article of claim 1, wherein at least a portion of the polymer composition has an etching, and wherein the etching is legible when observed from a distance of 0.3 meters without magnification after the exposure of the article to 100 cycles of hydrogen peroxide plasma sterilization.

10. The sterilized article of claim 9, wherein the etching is legible when observed from a distance of 0.3 meters without magnification after exposure of the article to 100 to 200 sterilization cycles, wherein each cycle is from 10 to 60 minutes at 20 to 55° C.

11. The sterilized article of claim 1, wherein the polymer composition comprises
   from 30 to 70 weight % of the polyphenylene ether sulfone; and
   from 70 to 30 weight % of the polyetherimide.

12. The sterilized article of claim 1, wherein the polymer composition comprises from 40 to 60 weight % of the polyphenylene ether sulfone; and from 60 to 40 weight % of the polyetherimide.

13. The sterilized article of claim 1, wherein the polymer composition comprises from 20 to 40 weight % of the polyphenylene ether sulfone; and from 80 to 60 weight % of the polyetherimide.

14. The sterilized article of claim 1, wherein the polyetherimide comprises repeating units of the formula

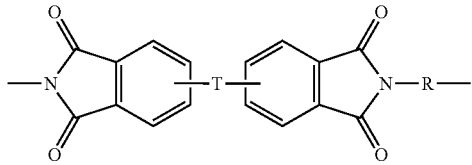

wherein

R is a divalent radical of the formulae

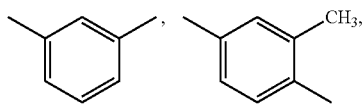

-continued

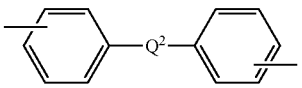

or combinations thereof wherein Q is selected from —O—, —S—, —C(O)—, —SO$_2$—, —SO—, and —C$_y$H$_{2y}$— wherein y is an integer from 1 to 5; and T is —O— or a group of the formula —O-Z-O— wherein the divalent bonds of the —O— or the —O-Z-O— group are in the 3,3', 3,4', 4,3', or the 4,4' positions or a divalent group of formula

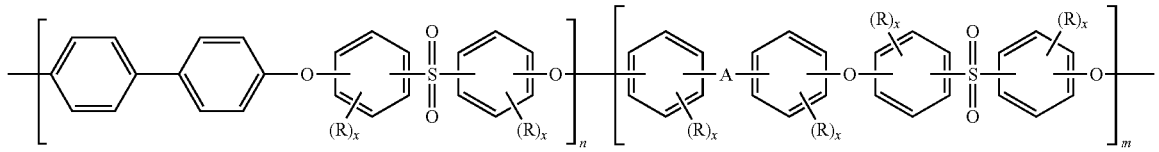

wherein Q$^2$ is selected from —O—, —S—, —C(O)—, —SO$_2$—, —SO—, and —C$_y$H$_{2y}$— wherein y is an integer from 1 to 5.

15. The sterilized article of claim 1, wherein the polyetherimide has less than 5 ppm of free bisphenol A.

16. The sterilized article of claim 1, wherein the polyphenylene ether sulfone is a copolymer of the following structure:

wherein n>m; and n+m is 25 to 1000,

R is selected from a C$_{1-8}$ alkyl, aryl, alkylaryl, alkoxy, halogen, and combinations thereof, x is 0 to 4, the aryl sulfone linkages are selected from 4,4' linkages, 3,3' linkages, 3,4' linkages, and combinations thereof, A is selected from —O—, —S—, —SO$_2$—, C$_{6-18}$ aryl, C$_{3-12}$ alkyl, and combinations thereof, and linkages of A to the aryl groups are selected from 4,4' linkages, 3,3' linkages, 3,4' linkages, and combinations thereof.

17. The sterilized article of claim 16, wherein each x is 0.

18. The sterilized article of claim 1, wherein the polyetherimide comprises less than 50 ppm amine end groups, the polyphenylene ether sulfone has less than 50 ppm hydroxyl groups, and the polyphenylene ether sulfone is methyl ether end-capped.

19. The sterilized article of claim 1, wherein the polymer composition further comprises, based on the weight of the polymer composition, 0.1 to 20.0 weight % of a colorant selected from rutile titanium dioxide, anatase titanium dioxide, coated titanium dioxide, passivated titanium dioxide, and encapsulated titanium dioxide, wherein the titanium dioxide has a particle size of from 0.1 to 10 micrometers.

20. The sterilized article of claim 19, wherein the polymer composition further comprises a colorant selected from carbon black, solvent red 52, solvent violet 36, solvent violet 13, pigment brown 24, pigment blue 29, pigment blue 15:4, or combinations thereof.

21. The sterilized article of claim 1, wherein the polymer composition further comprises, based on the weight of the polymer composition, at least 0.01 weight % of a phosphorous containing stabilizer having a molecular weight of at least 300 Daltons.

22. The sterilized article of claim 21, wherein the phosphorous stabilizer is selected from aryl phosphites and aryl phosphonates.

23. The sterilized article of claim 1, wherein the polymer composition further comprises, based on the weight of the polymer composition, at least 0.05 weight % of a mold release agent selected from C6 to C36 alkyl carboxylic esters, C6 to C36 alkyl carboxylic acids, C6 to C36 alkyl carboxylic acid salts, C6 to C36 alkyl amides, and polyolefins.

24. The sterilized article of claim 1, wherein the article is selected from a molded part, sheet, slab, profile, film, and fiber.

25. The sterilized article of claim 24, wherein the article is selected from a medical device, dental device, surgical device, sterilization device, decontamination device, food handling device, food preparation device, beverage handling device, beverage preparation device, or a component thereof.

26. The sterilized article of claim 25, wherein the article is selected from a container, a syringe body, a tray, an animal cage, an endoscope, a ureteroscope, a catheter, a clamp, a cable, a telescope, forceps, scissors, and a drill.

27. The sterilized article of claim 1, wherein the article further comprises a biocidal additive component.

28. The sterilized article of claim 27, wherein the biocidal additive component is selected from metals, inorganic compounds, and organic compounds.

29. The sterilized article of claim 27, wherein the biocide is selected from germicides, antibiotics, antibacterials, antivirals, antifungals, antiprotozoals, antiyeasts, antialgals, antiparasites, and combinations thereof.

30. The sterilized article of claim 1, wherein the tensile strength at yield of the article after 150 hydrogen peroxide plasma sterilization cycles is at least 12,000 psi (82.8 MPa).

31. A sterilized article comprising a sterilized polymer composition, having an as molded color treated with a member selected from hydrogen peroxide plasma, hydrogen peroxide vapor, and combinations thereof, the polymer composition comprising
a) from 80 to 20 weight % of a polyphenylene ether sulfone; the polyphenylene ether sulfone having the formula

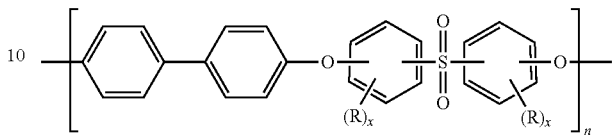

wherein
n is 25 to 1000,
R is selected from $C_{1-8}$ alkyl, aryl, alkyl aryl, alkoxy, halogen, and combinations thereof,
x is 0 to 4, and
the aryl sulfone linkages are selected from 4,4' linkages, 3,3' linkages, 3,4' linkages, and combinations thereof; and
b) from 20 to 80 weight % of a polyetherimide;
wherein after exposure to 150 cycles of the hydrogen peroxide plasma sterilization using a mixture of hydrogen peroxide vapor and hydrogen peroxide plasma for 30 minutes at 20 to 55° C., the color of the polymer composition exhibits a color shift of delta E of 10 units or less relative to the as molded color of the polymer composition color before the first hydrogen peroxide plasma sterilization cycle;
wherein delta E is measured in accordance with ASTM D2244-05 and an article molded from the composition (i) initially also exhibits a multiaxial impact energy of greater than or equal to 45 ft-lbs (61 Joules) and (ii) after 150 cycles hydrogen peroxide plasma exposure has a multiaxial impact energy of greater than or equal to 20 ft-lbs (27 Joules) and multiaxial impact energy is determined according to ASTM D5628-10 at 23° C.;
wherein at least a portion of the polymer composition has an etching, and wherein the etching is legible when observed from a distance of 0.3 meters without magnification after the exposure of the article to 100 cycles of hydrogen peroxide plasma sterilization.

* * * * *